US010494684B2

(12) United States Patent
Penet et al.

(10) Patent No.: US 10,494,684 B2
(45) Date of Patent: Dec. 3, 2019

(54) BACILLUS COMPOSITIONS AND USES THEREOF

(71) Applicant: BIO-CAT, INC., Troy, VA (US)

(72) Inventors: Christopher S. Penet, Manakin Sabot, VA (US); Sebhat Gebrechristos, New Hope, MN (US); Caroline Helen Best, Palmyra, VA (US); Deborah S. Winetzky, Charlottesville, VA (US); Robert Daniel Little, Jr., Charlottesville, VA (US); Jessica Spears, Minnetonka, MN (US); Christopher Schuler, Charlottesville, VA (US)

(73) Assignee: BIO-CAT, INC., Troy, VA (US)

(*) Notice: Subject to any disclaimer, the term of this patent is extended or adjusted under 35 U.S.C. 154(b) by 0 days.

(21) Appl. No.: 15/722,915

(22) Filed: Oct. 2, 2017

(65) Prior Publication Data

US 2018/0094327 A1 Apr. 5, 2018

Related U.S. Application Data

(60) Provisional application No. 62/403,467, filed on Oct. 3, 2016.

(51) Int. Cl.
*A61K 39/02* (2006.01)
*A61K 39/07* (2006.01)
*A61K 39/00* (2006.01)
*C12R 1/125* (2006.01)
*A23L 7/143* (2016.01)
*A21D 13/40* (2017.01)
*A21D 13/44* (2017.01)
*A23F 3/16* (2006.01)
*A23G 9/36* (2006.01)
*A61K 9/00* (2006.01)
*A61K 35/742* (2015.01)
*A61K 35/745* (2015.01)
*A61K 35/747* (2015.01)
*C11D 3/38* (2006.01)
*C11D 3/48* (2006.01)

(52) U.S. Cl.
CPC .............. *C12R 1/125* (2013.01); *A21D 13/40* (2017.01); *A21D 13/44* (2017.01); *A23F 3/16* (2013.01); *A23G 9/36* (2013.01); *A23L 7/143* (2016.08); *A61K 9/0056* (2013.01); *A61K 9/0095* (2013.01); *A61K 35/742* (2013.01); *A61K 35/745* (2013.01); *A61K 35/747* (2013.01); *C11D 3/381* (2013.01); *C11D 3/48* (2013.01); *A23V 2002/00* (2013.01)

(58) Field of Classification Search
CPC ......... A61K 39/00; A61K 39/07; A61K 39/09

USPC ............................................ 424/234.1, 246.1
See application file for complete search history.

(56) References Cited

U.S. PATENT DOCUMENTS

| 4,110,477 | A | 8/1978 | Naruse et al. |
| 6,162,635 | A | 12/2000 | Lawler et al. |
| 6,461,607 | B1 | 10/2002 | Farmer |
| 8,697,055 | B2 | 4/2014 | Farmer |
| 8,940,679 | B2 | 1/2015 | Jabrane |
| 9,144,588 | B2 | 9/2015 | Rubio et al. |
| 9,247,757 | B2 | 2/2016 | Schmidt et al. |
| 9,301,982 | B2 | 4/2016 | Lefkowitz |
| 2013/0184196 | A1 | 7/2013 | Brooke |
| 2015/0164087 | A1 | 6/2015 | Kang |
| 2016/0029666 | A1 | 2/2016 | Carpenter et al. |

FOREIGN PATENT DOCUMENTS

CN 102191189 A 9/2011

OTHER PUBLICATIONS https://bcmicrobials.com/applications/dietary-supplements/, accessed Nov. 12, 2018.*
"Bacillus subtilis", Chemex, Cleaning and Hygiene Specialists, pp. 1-4, Retrieved Jul. 21, 2016.
"Dietary Supplements", OPTI-BIOME Bacillus subtilis MB40, www.bcmicrobials.com, BIO-CAT Microbials, Aug. 2016.
"Functional Protein Powders in Food and Sports Nutrition Drink Mixes", OPTI-BIOME Bacillus subtilis MB40, www.bcmicrobials.com, BIO-CAT Microbials, Aug. 2016.
"Introduction", OPTI-BIOME Bacillus subtilis MB40, www.bcmicrobials.com, BIO-CAT Microbials, pp. 1-5, May 2016.
"Spore Handling Guidance", OPTI-BIOME Bacillus subtilis MB40, www.bcmicrobials.com, BIO-CAT Microbials, Mar. 2016.
Berry, Donna, "Working behind the scenes", Food Business News, pp. 1-7, Retrieved Jul. 21, 2016.
Brochure, OPTI-BIOME Bacillus subtilis MB40, www.bcmicrobials.com, BIO-CAT Microbials, pp. 1-2, Aug. 2016.
Cote, J. et al., "Probiotics in Bread and Baked Products: A New Product Category", AACC International, Cereal Foods World 28(6): 293, Nov./Dec. 2013, pp. 1-2.
Gorton, Laurie, "Working with Probiotics" Baking Business, pp. 1-5, Retrieved Jul. 21, 2016.
Permpoonpattana et al., "Evaluation of Bacillus subtilis strains as probiotics and their potential as a food ingredient", Washington Academic Publications, Beneficial Microbes, Jun. 2012, 3(2): pp. 127-135.
Vandini et al., "Hard Surface Biocontrol in Hospitals Using Microbial-Based Cleaning Products", PLOS ONE, vol. 9, Issue 9, e108598, Sep. 2014, pp. 1-13.

* cited by examiner

*Primary Examiner* — Rodney P Swartz
(74) *Attorney, Agent, or Firm* — Arent Fox LLP

(57) ABSTRACT

A spore-forming *Bacillus* species, and more particularly, a *Bacillus subtilis* strain identified as MB40 is provided. Compositions comprising the MB40 strain, methods of making products comprising the same, and methods of using the same are also provided.

23 Claims, 16 Drawing Sheets

Survivability of *B. subtilis* MB40 in Blended Whey Flour

Survivability of *B. subtilis* MB40 in Blended Peanut Flour

| Factor A (pH) | Factor B (% solid) |
|---|---|
| 2 | 30 |
| 4 | 50 |
| 6 | 70 |

BACILLUS COMPOSITIONS AND USES THEREOF

CROSS-REFERENCE TO RELATED APPLICATION

This application claims the benefit of U.S. Provisional Application No. 62/403,467, which was filed on Oct. 3, 2016, the contents of which is incorporated herein by reference in its entirety.

TECHNICAL FIELD

A novel spore-forming *Bacillus* species, and more particularly, a *Bacillus subtilis* strain identified as MB40 is provided. The disclosure also relates to compositions comprising the MB40 strain, methods of making products comprising the same, and methods of using the same.

BACKGROUND

The term "probiotic" is generally used to refer to live microorganisms that provide health benefits or other positive effects when administered (e.g., by ingestion of a probiotic-containing food or dietary supplement). Probiotics may benefit a host directly, e.g., by excreting compounds that interact with the host's gastrointestinal system or by expressing useful enzymes that are absent from or insufficiently expressed by the host. Probiotics may also benefit the host indirectly by interacting with other gut flora in a manner that has a beneficial effect on the host, e.g., by displacing pathogenic bacteria. The precise nature of these interactions is often poorly understood due to the complexity of the gastrointestinal system and the gut microbiome. However, the probiotic nature of a microorganism can be evaluated based on the detection and measurement of its effects on a host regardless of whether the precise mechanism underlying the effects remains unknown.

In recent years, probiotics have emerged as a promising target for therapeutics and dietary supplements intended to promote positive gastrointestinal health and other benefits. Probiotic microorganisms have been identified in various genera, including *Lactobacillus, Bifidobacterium, Propionibacterium, Escherichia*, and *Saccharomyces*, with *Lactobacillus* strains being the most well characterized and commercial significant probiotics.

Traditionally, probiotics suitable for human consumption have been confined to fermented foods and dairy compositions (e.g., miso, tempeh, kefir, buttermilk, cheese, and yogurt), which provide an environment suitable to allow a sufficient amount of the probiotic bacteria to survive during typical storage conditions. More recently, dietary supplements (e.g., tablets, sachets and other delivery vehicles) have been developed which are suitable for at least some probiotics. However, survivability concerns limit the widespread use of many probiotics. In particular, many of the currently known probiotics cannot survive high temperatures for extended periods of time, substantially limiting the types of foods and supplements that may be used as a delivery vehicle for these probiotics.

SUMMARY OF VARIOUS EMBODIMENTS

In a general aspect, the present disclosure relates to a novel, non-naturally occurring, spore-forming *Bacillus* species, and more particularly, to *Bacillus subtilis* MB40, a sample of which has been deposited under ATCC Accession Number PTA-122264. *Bacillus subtilis* MB40 is capable of surviving extended exposure to high temperatures and stable when stored for prolonged periods (e.g., as a spore). As such, in one aspect, the disclosed bacteria overcomes limitations of prior bacterial species used as probiotics.

In other general aspects, compositions, supplements and other delivery vehicles comprising the MB40 strain are disclosed. In particular aspects, compositions, such as food products, beverage products, cleaning products, and dietary supplements, comprising the MB40 strain are provided.

In some aspects, a food product comprising MB40 cells and/or spores is provided. The food product may be probiotic (e.g., comprising MB40 in an amount effective to provide a health benefit or other beneficial effect when administered to a human or animal). In some aspects, the food product is a muffin, pancake, bread, cake, biscuit, pancake, or waffle. The MB40 may be present at a concentration of at least $1\times10^6$, $1\times10^7$, $1\times10^8$, $1\times10^9$, or $2\times10^9$ colony-forming units (CFUs)/gram, or an amount of at least $1\times10^6$, $1\times10^7$, $1\times10^8$, $1\times10^9$, or $2\times10^9$ CFUs per food product or serving of the food product. The food product may comprise flour, and/or at least one other probiotic, such as a species of *Lactobacillus* or *Bifidobacterium*.

In other aspects, the disclosure provides beverages (e.g., tea, juice, dairy product, soda, coffee, sports drink, or energy drink) comprising MB40 at a concentration of at least $1\times10^6$, $1\times10^7$, $1\times10^8$, $1\times10^9$, or $2\times10^9$ CFUs/gram. The beverage may comprise at least one other probiotic, such as a species of *Lactobacillus* or *Bifidobacterium*. The beverage may also comprise one or more of the following additives: natural or artificial sweeteners (e.g., sugar or sucralose), soluble fiber (e.g. pectin), insoluble fiber, flavoring agents, colorants/dyes, stabilizers, preservatives, oils (e.g., fatty acids), emulsifiers, vitamins, minerals, amino acids, peptides, and/or proteins.

In other aspects, the disclosure provides dietary supplements (e.g., a powder, tablet, pill, sachet, capsule, or suspension) comprising MB40. The MB40 may be present at a concentration of at least $1\times10^6$, $1\times10^7$, $1\times10^8$, $1\times10^9$, $5\times10^9$, or $1\times10^{10}$ CFUs/gram. The dietary supplement may comprise at least one other probiotic, such as is a species of *Lactobacillus* or *Bifidobacterium*. In some aspects, the supplement may include spray dried MB40 spores. The dietary supplement may also comprise one or more of the following additives: natural or artificial sweeteners (e.g., sugar or sucralose), soluble fiber (e.g. pectin), insoluble fiber, flavoring agents, colorants/dyes, stabilizers, preservatives, anti-caking agents, vitamins, minerals, amino acids, peptides, and/or proteins.

In other aspects, the disclosure provides pet food compositions comprising MB40. These compositions may be generally formulated similarly to the disclosed food products and beverages. The pet food may be a dry mixture, a wet mixture, or a liquid. In some aspects, it may comprise one or more fatty acids, free amino acids, or protein, and optionally one or more additional probiotics.

In other aspects, the disclosure provides cleaning and/or antimicrobial compositions comprising MB40. In some aspects, the compositions may comprise MB40 suspended in a solvent with one or more of the following: an ionic or nonionic surfactant, an antimicrobial or antifungal disinfectant, a salt, and an oxidizing agent. In other aspects, the cleaning and/or antimicrobial compositions comprise one or more additional bacteria, such as members of the following genera: *Bacillus* (e.g., *B. subtilis, B. coagulans, B. lentis, B. cereus, B. clausii, B. pumilus, B. licheniformis, B. polymyxa, B. methanolicus, B. amyloliquefaciens, B. pasteurii, B.*

*laevolacticus, B. megaterium*), *Lactobacillus* (e.g., *L. acidophilus, L. casei, L. reuteri, L. helveticus, L. rhamnosus, L. plantarum*), *Brevibacillus* (e.g., *B. laterosporus*), *Bifidobacterium* (e.g., *B. bifidum, B. infantis, B. breve, B. longum*), *Pseudomonas* (e.g., *P. aeruginosa, P. alkanolytica, P. dentrificans*), *Arthrobacter* (e.g., *A. paraffineus, A. petroleophagus, A. rubellus*), *Enterobacter* (e.g., *E. cloacae*), *Streptococcus* (e.g., *S. thermophilus*), or *Enterococcus* (e.g. *E. faecium*). The MB40 may be present as live cells and/or spores at a concentration of at least $1\times10^6$, $1\times10^7$, $1\times10^8$, $1\times10^9$, or $1\times10^{10}$ CFUs/gram.

In further aspects, the disclosure provides methods of making and using compositions comprising MB40. For example, the compositions may be used to clean or disinfect a surface or area. In other aspects, methods of using MB40 to provide a health benefit or other beneficial effect to a human or animal are disclosed (e.g., methods of reducing, modulating, or maintaining the level of total cholesterol, triglycerides, and/or glucose in a human). In some aspects, the methods are directed to reducing gastrointestinal symptoms (e.g., one or more of bloating, upper abdominal pain, flatulence, and/or diarrhea).

Additional aspects will be readily apparent to one of skill in light of the totality of the disclosure.

BRIEF DESCRIPTION OF THE DRAWINGS

FIG. 13(*d*) summarizes the survivability results for *B. subtilis* MB40 stored in liquid medium at various pH and percent-solid levels during a 10-month period.

FIG. 15(*b*) is a chart illustrating the *B. subtilis* MB40 spore viability results summarized in FIG. 15(*a*).

DETAILED DESCRIPTION OF VARIOUS EMBODIMENTS

Figure 1:
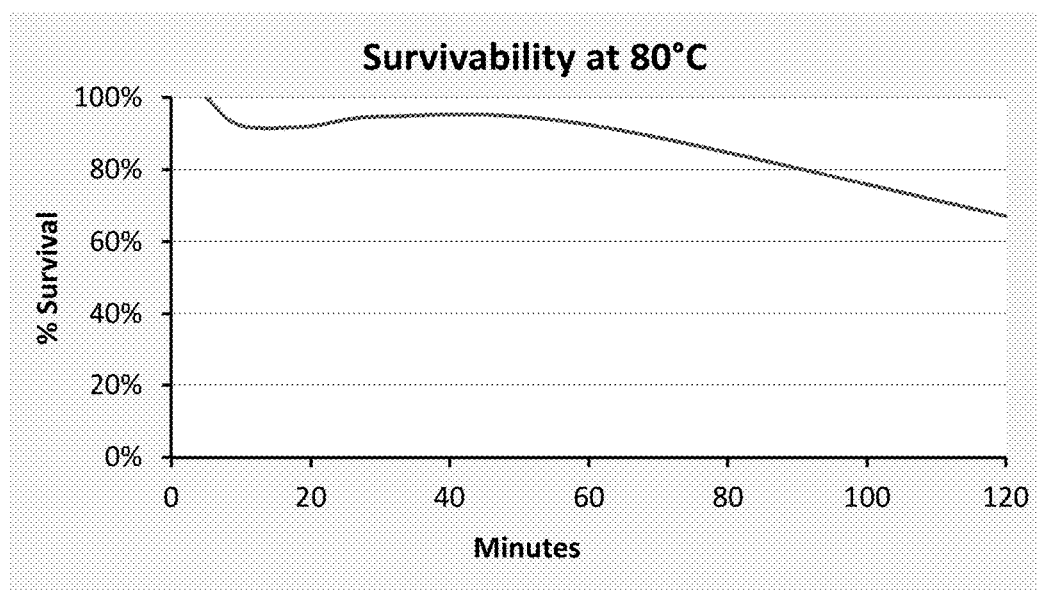
FIG. 1 is a graph illustrating survivability of *B. subtilis* MB40 at 80° C.

The present disclosure relates to a novel spore-forming *Bacillus* species, and more particularly, to a *B. subtilis* MB40 strain which has been deposited as ATCC Accession Number PTA-122264. Compositions comprising *B. subtilis* MB40 and methods of making and using the same are also provided.

The microbiome of a typical human gastrointestinal tract is understood to contain approximately $10^{14}$ cells, comprising several hundred different bacterial species. Interactions between the gut flora and the host's immune and gastrointestinal systems are believed to play a fundamental role in influencing physiological and homeostatic functions of the host. In essence, the microbiome may be considered to function as a separate organ to some extent. Disruption of the complex interplay between the host's systems and the microbiome can lead to the development of diseases and negative physiological effects. For example, pathogenic bacteria may displace normal gut flora, resulting in inflammation and/or other gastrointestinal diseases or disorders. Similarly, a host's microbiome may lack a beneficial microorganism normally part of the commensal gut bacteria, whether due to natural processes or due to exposure to an antibiotic. In each case, an imbalance exists in the normal gut flora, resulting in detrimental effects for the host.

In order to correct this imbalance, the host may be administered a probiotic food composition, dietary supplement, or other suitable vehicle comprising the probiotic in a quantity sufficient to support colonization or otherwise correct the imbalance. However, due to survivability issues, current probiotics are limited to a relatively narrow range of foods, beverages, and dietary supplement dosage forms. In particular, current probiotics are generally unsuitable for foods, beverages, and dietary supplements exposed to high temperatures or varying pH conditions. As a result, many types of probiotic compositions (e.g., baked goods, powdered supplements) and other similar products are not practical using currently available probiotics.

The *B. subtilis* MB40 strain disclosed herein addresses these and other shortcomings. For example, probiotic compositions having excellent survivability across a wide range of temperatures and pH levels are provided. In particular, the MB40 strain is a particularly well-suited probiotic useful in foods, such as baked goods, and other food products or supplements exposed to high temperatures during production or storage. The MB40 strain is also useful as, among other things, a cleaning product, and more generally, as part of a cleaning treatment (e.g., for floors or drains), where temperature and/or pH may present a concern for other less hardy microorganisms.

The MB40 strain is a non-naturally occurring, Gram-positive, spore forming, rod-shaped facultative anaerobe. Initial characterization assays indicate that MB40 is catalase-positive, and that it retains the ability to express amylase, cellulase, lipase, protease, urease, and xylanase to varying extents. Products featuring *Bacillus subtilis* MB40 are currently marketed under the OPTI-BIOME® brand by BIO-CAT Microbials.

The MB40 strain described herein was derived from *B. subtilis* DSM-10 (DSMZ; Leibniz Institute DSMZ—German Collection of Microorganisms and Cell Cultures Inhoffenstraße 7B 38124 Braunschweig, Germany). *B. subtilis* is a ubiquitous bacterium commonly found in nature and present in the food supply. *B. subtilis* is not considered pathogenic or toxigenic to humans, animals, or plants and, for example, at least one *B. subtilis* strain has been classified by the U.S. Food and Drug Administration as Generally Recognized As Safe (GRAS), i.e., GRN 399 and GRN 526 for *B. coagulans*. The parent strain of MB40 (*B. subtilis* DSM-10) was originally isolated from soil, purified, and cultured under highly-controlled fermentation conditions over a number of years. DNA ribotyping analysis and full genome sequence analysis has shown that MB40 strain has a 99% similarity to the parent strain. Therefore, the MB40 strain is a variant of *B. subtilis* DSM-10.

Figure 2:
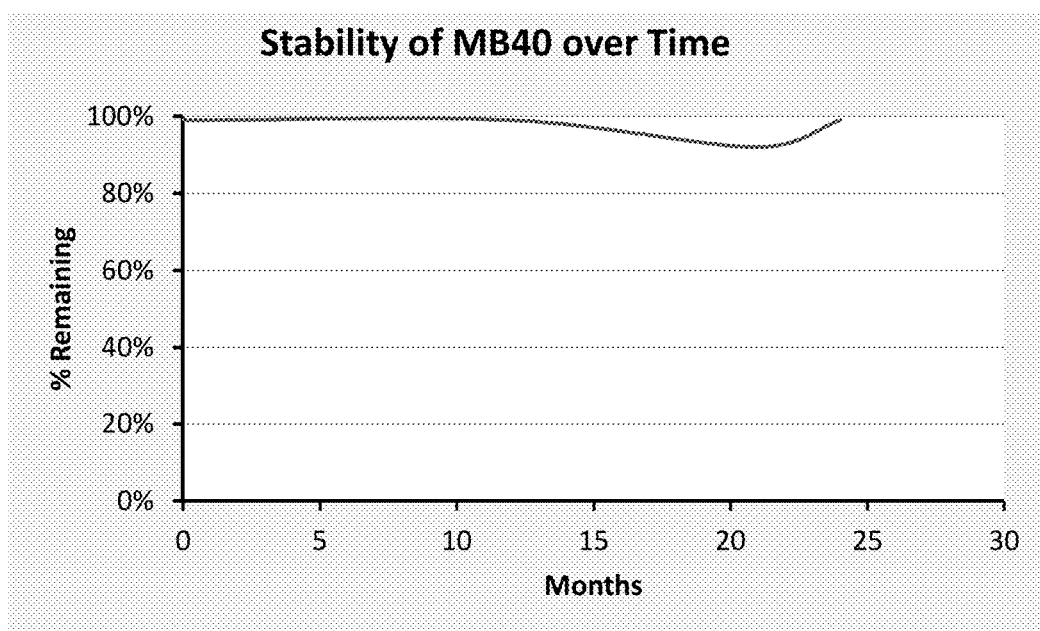
FIG. 2 is a graph illustrating survivability of *B. subtilis* MB40 at room temperature.
Figure 3:
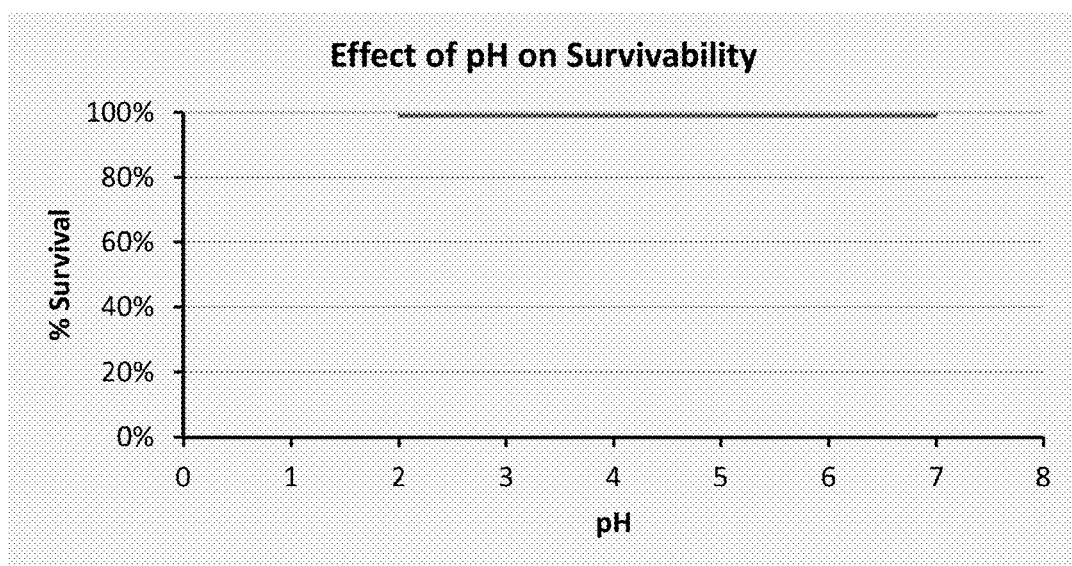
FIG. 3 is a graph illustrating survivability of *B. subtilis* MB40 across various pH levels.

The MB40 strain is highly stable when exposed to high temperatures and for extended periods of time at room temperature. For example, FIG. 1 illustrates that >60% of MB40 spores remain viable after 120 minutes at 80° C. Similarly, FIG. 2 illustrates that >90% of MB40 spores remain viable when stored at room temperature for 25 months. Moreover, as shown in FIG. 3, the MB40 strain is highly tolerant as to changes in pH, with a 100% survival rate for MB40 spores exposed to solutions spanning pH 2 to pH 7. To measure survival, equal concentrations of MB40 were suspended in solutions at the pH levels shown in FIG. 3 for 4 hours at 37° C. The surviving concentration was determined by a subsequent total plate count (TPC) assay. As a result, the MB40 strain is a good candidate for use in products, such as food and cleaning products, capable of withstanding high temperatures, exposure to room temperature for long periods of time, and/or pH changes.

Food Products, Beverages and Dietary Supplements Comprising MB40 Cells and/or Spores MB40 cells and/or spores may be included in a variety of food products, beverages, and dietary supplements in order to provide positive health effects or other benefits. In select aspects, the disclosure provides compositions comprising MB40 cells, spores, or a combination thereof capable of surviving exposure to heat and/or long periods of time at room temperature (e.g., at least 24 months). For example, in some aspects the disclosure provides compositions (e.g., food and beverage products, dietary supplements) comprising MB40 cells and/or spores in an amount effective to provide a health benefit to a consumer of a food product, beverage or supplement.

In some aspects, the composition comprising MB40 cells and/or spores is a food product, such as a baked good. Exemplary baked goods include, but are not limited to, muffins, breads, waffles, cakes, biscuits, cookies, pies, tarts, pastries, candy/energy bars, granola, cereal, crackers. In select aspects, the composition includes any baked good that comprises flour, or which is prepared by baking (e.g., by exposure to dry heat). Other baked goods that may serve as a vehicle for the MB40 include pizza, pasta, corn or potato chips, dehydrated fruits or vegetables. In view of MB40's tolerance for high temperatures, most baked goods can serve as a delivery system for MB40, providing a variety of new probiotic food options unavailable to many probiotics known in the art.

In some aspects, the MB40 cells and/or spores may comprise between about 0.001% to about 10% by weight of the food product (e.g., a baked good, dietary supplement, or beverage). In other exemplary aspects, the MB40 cells and/or spores may comprise between about 0.01% and about 10% by weight of the food product, dietary supplement, or beverage. Heating and processing will affect the amount or concentration of MB40 is a final product. For example, the amount or concentration of MB40 cells and/or spores present in a baked good will depend on both the amount of colony-forming units applied to the pre-baked composition and parameters related to the baking step (e.g., time, temperature, moisture levels). In some aspects, the MB40 cells and/or spores may comprise at least about 0.001%, 0.01%, 0.1%, 1%, or 10% by weight of the food product, or a range between about 0.001% to about 0.01%, about 0.01% to about 0.1%, about 1% to about 10%, about 10% to about 20%, or ≥20% by weight of the food product. It is further understood that in still other aspects, the amount of MB40 cells and/or spores may comprise a minimum and/or a maximum percentage amount selected from any of the aforementioned ranges.

In some aspects, the composition may comprise a mixture or batter for preparing a food product that will be baked (e.g., bread, muffins), fried, or otherwise heated, wherein the mixture comprises MB40 cells and/or spores. The composition may be formulated such that a given percentage (e.g., at least 10%, 20%, 30%, 40%, 50%, 60%, 70%, 80%, or 90%) of the MB40 cells and/or spores present in a given amount or volume of the starting mixture or batter remain viable in the final baked, fried, or otherwise heated food product. In some aspects, the composition may be formulated such that about 10% to about 20%, about 20% to about 30%, about 30% to about 40%, about 40% to about 50%, about 50% to about 60%, about 60% to about 70%, about 70% to about 80%, about 80% to about 90%, or ≥90% of the MB40 cells and/or spores present in a given amount or volume of the starting mixture or batter remain viable in the final baked, fried, or otherwise heated food product. It is further understood that in still other aspects, the percentage of viable cells may be a range that includes a minimum and/or a maximum percentage amount selected from any of the aforementioned ranges.

The following are exemplary food products comprising the MB40 strain. This is a non-exhaustive list, and merely includes various classes of foods and beverages that may serve as a delivery vehicle for MB40 cells and/or spores.

| Food Category |
| --- |
| (1) Baked goods and baking mixes, including all ready-to-eat and ready-to-bake products, flours, and mixes requiring preparation before serving. |
| (2) Beverages, alcoholic, including malt beverages, wines, distilled liquors, and cocktail mix. |
| (3) Beverages and beverage bases, nonalcoholic, including only special or spiced teas, soft drinks, coffee substitutes, and fruit and vegetable flavored gelatin drinks. |

| Food Category |
| --- |
| (4) Breakfast cereals, including ready-to-eat and instant and regular hot cereals.
(5) Cheeses, including curd and whey cheeses, cream, natural, grating, processed, spread, dip, and miscellaneous cheeses.
(6) Chewing gum, including all forms.
(7) Coffee and tea, including regular, decaffeinated, and instant types.
(8) Condiments and relishes, including plain seasoning sauces and spreads, olives, pickles, and relishes, but not spices or herbs.
(9) Confections and frostings, including candy and flavored frostings, marshmallows, baking chocolate, and brown, lump, rock, maple, powdered, and raw sugars.
(10) Dairy product analogs, including nondairy milk, frozen or liquid creamers, coffee whiteners, toppings, and other nondairy products.
(12) Fats and oils, including margarine, dressings for salads, butter, salad oils, shortenings and cooking oils.
(16) Fresh fruit juices, including only raw fruits, citrus, melons, and berries, and home prepared "ades" and punches made therefrom.
(20) Frozen dairy desserts and mixes, including ice cream, ice milks, sherbets, and other frozen dairy desserts and specialties.
(21) Fruit and water ices, including all frozen fruit and water ices.
(22) Gelatins, puddings, and fillings, including flavored gelatin desserts, puddings, custards, parfaits, pie fillings, and gelatin base salads.
(23) Grain products and pastas, including macaroni and noodle products, rice dishes, and frozen multicourse meals, without meat or vegetables.
(25) Hard candy and cough drops, including all hard type candies.
(26) Herbs, seeds, spices, seasonings, blends, extracts, and flavorings, including all natural and artificial spices, blends, and flavors.
(28) Jams and jellies, commercial, including only commercially processed jams, jellies, fruit butters, preserves, and sweet spreads.
(30) Milk, whole and skim, including only whole, lowfat, and skim fluid milks.
(31) Milk products, including flavored milks and milk drinks, dry milks, toppings, snack dips, spreads, weight control milk beverages, and other milk origin products.
(32) Nuts and nut products, including whole or shelled tree nuts, peanuts, coconut, and_nut and peanut spreads.
(33) Plant protein products, including the National Academy of Sciences/National Research Council "reconstituted vegetable protein" category, and meat, poultry, and fish substitutes, analogs, and extender products made from plant proteins.
(35) Processed fruits and fruit juices, including all commercially processed fruits, citrus, berries, and mixtures; salads, juices and juice punches, concentrates, dilutions, "ades", and drink substitutes made therefrom.
(36) Processed vegetables and vegetable juices, including all commercially processed vegetables, vegetable dishes, frozen multicourse vegetable meals, and vegetable juices and blends.
(37) Snack foods, including chips, pretzels, and other novelty snacks.
(38) Soft candy, including candy bars, chocolates, fudge, mints, and other chewy or nougat candies.
(40) Soups and soup mixes, including commercially prepared meat, fish, poultry, vegetable, and combination soups and soup mixes.
(41) Sugar, white, granulated, including only white granulated sugar.
(42) Sugar substitutes, including granulated, liquid, and tablet sugar substitutes.
(43) Sweet sauces, toppings, and syrups, including chocolate, berry, fruit, corn syrup, and maple sweet sauces and toppings. |

In some aspects, the disclosure provides probiotic compositions (e.g., food products, beverages, or dietary supplements) comprising MB40 cells and/or endospores that remain shelf stable for long periods of time, such as 4 months, 6 months, 12 months, 18 months, 24 months, or more than 24 months at, for example, room temperature. For example, spores added to a granola bar during processing may remain viable for extended periods of time while the bar is stored on a store shelf at room temperature. Compositions may be formulated to increase or decrease stability (e.g., by varying moisture levels). In select aspects, the compositions are formulated to retain a particular percentage of viable cells after a given amount of time stored at room temperature (e.g., at least 50%, 60%, 70%, 80%, or 90%).

In some aspects, the food or dietary supplement comprising the MB40 cells and/or spores may be a spray-dried product (e.g., wherein either the entire product or the MB40 cells and/or spores have been subjected to a spray drying process). Spray drying is a method of producing a dry powder from a liquid or slurry by rapidly drying with a hot gas, and is a preferred method of drying many thermally-sensitive materials, such as foods and pharmaceuticals. Spray drying of the MB40 cells and/or spores may be used to further enhance the survivability of the MB40 in the delivery vehicle. For example, a spray drying step during processing may generate a dry mixture for a food product that displays a higher degree of stability at room temperature than a comparable mixture lacking this spray drying step. Various methods of spray drying are known in the art to be suitable for bacteria and may be used or adapted for use with MB40 cells. For example, spray drying protocols may include carbohydrates, such as polysaccharides or polyols, that enhance preservation by preventing crystallization during the drying step. Similarly, methods known in the art allow for spray drying of bacteria in the presence of inactive agents, such as plasticizers and glidants, so as to produce a particle that provides controlled release after ingestion. It is contemplated that the MB40 cells and/or spores disclosed herein may be spray dried by any methods known in the art suitable for bacteria, particularly methods suitable for *B. subtilis*.

The MB40 may be included in a beverage composition, whether as vegetative cells, spores, or a combination thereof.

In some aspects, the beverage is a hot beverage (e.g., tea, coffee), while in others it is a cold beverage (juice, soda). MB40 spores and/or cells may be added to the beverage during processing by a manufacturer, or by an end user (e.g., by a consumer adding a dry mixture comprising MB40 spores and optionally other nutrients to a water or another liquid to prepare a probiotic meal replacement beverage). In other aspects, the beverage product comprises MB40 and one or more of the following additives: natural or artificial sweeteners (e.g., sugar or sucralose), soluble fiber (e.g. pectin), insoluble fiber, flavoring agents, colorants/dyes, stabilizers, preservatives, oils (e.g., fatty acids), emulsifiers, vitamins, minerals, amino acids, peptides, and/or proteins. In view of MB40's broad survivability profile across different temperatures and pH levels, it is understood that MB40 cells or spores may be added to the numerous beverages currently sold or prepared for human consumption.

The MB40 may be included in a dietary supplement, whether as vegetative cells, spores, or a combination thereof. The dietary supplement may be a powder, tablet, pill, sachet, capsule, or suspension. Exemplary dietary supplements include products that may be added to foods or drinks, such as protein powders. In some aspects, the dietary supplement comprises MB40 and one or more of the following additives: natural or artificial sweeteners (e.g., sugar or sucralose), soluble fiber (e.g. pectin), insoluble fiber, flavoring agents, colorants/dyes, stabilizers, preservatives, anti-caking agents, vitamins, minerals, amino acids, peptides, and/or proteins. In other aspects, the dietary supplement is a composition, such as a capsule, comprising MB40 that can be taken with or without food or drink.

The amount of MB40 cells and/or spores added to a food product, beverage, or dietary supplement may be varied to ensure that a desired amount of viable cells remain in the product administered to an end user. This amount may be selected to ensure that the amount present is sufficient to provide a given benefit to the user, such as a reduction in gastrointestinal symptoms. The amount may also be varied based upon an expected administration regimen (e.g., a dietary supplement comprising MB40 may be marketed for daily use). Daily use may include a once-daily, twice-daily, or several times daily. In alternative aspects, once-weekly, twice-weekly and other weekly or longer regimens are possible. Specific regimens and amounts (or concentrations) of the MB40 administered are dictated by the particular application and the parameters needed to achieve an effective amount for a health benefit or other positive effect.

The concentration of MB40 in a given food product, beverage, or dietary supplement may also be varied, for example to provide an amount effective to achieve a given health benefit. In some aspects, the concentration of MB40 in the food product, beverage, or dietary supplement is about $10^2$ to $10^{10}$ CFUs of MB40 per gram. In other aspects, the concentration may comprise $10^4$ to $10^8$ CFU/g, or $10^6$ to $10^7$ CFU/g. In other aspects, the concentration may comprise $1\times10^9$ to $1\times10^{10}$ CFU/g or $1\times10^9$ to $1\times10^{11}$ CFU/g. In some aspects, the amount or concentration of MB40 may be determined on a per unit basis (e.g., up to $1\times10^9$ CFU or $2\times10^9$ CFU per serving). In some aspects, the concentration may be measured on a per food product, beverage product, or dietary supplement basis. In other aspects, the amount of MB40 is determined on a daily or weekly basis, such as $1$-$10\times10^9$ CFUs/day, or $1$-$2\times10^{10}$ CFUs/week.

The concentration of MB40 in a given food product, beverage, or dietary supplement may also be varied, for example to provide an amount effective to achieve a given health benefit. When administered as a dietary supplement, the daily intake level for MB40 may be approximately $1\times10^9$ to $1\times10^{10}$ CFUs of MB40/day, though the amount may vary within that range based upon the particular application and intended effect (e.g., $5\times10^9$ CFU/day). Dietary supplements may be formulated to include an amount of MB40 CFUs sufficient to achieve any of these daily intake amounts when administered per instructions or expected use by a consumer (e.g., a twice-daily supplement may comprise $5\times10^9$ CFUs per serving in order to reach a recommended daily intake of $1\times10^{10}$). Amounts will vary depending on whether the supplement is once-daily, twice-daily, etc. and the total daily intake recommended for the individual or animal. When administered as a food product, in some aspects the product may be formulated to satisfy a recommended daily intake of up to $2\times10^9$ CFUs. For example, a food or beverage product expected to be consumed at a rate of two servings per day may be formulated to comprise up to $1\times10^9$ CFUs per serving. Alternatively, if a food or beverage is typically consumed by weight (or volume) and not in discrete servings, the formulation of a food product may be designed to provide a suitable concentration of MB40 per gram or unit of volume. For example, if a consumer typically ingests 10 grams of a particular food product per day, the product may be formulated to include approximately to $2\times10^8$ CFUs/gram. Other formulations may take into account a higher or lower expected number of servings or amount consumed per day, or based on the particular application. for example, when administered as a protein powder or sports nutrition drink, in some aspects the MB40 may be included at approximately $1\times10^9$ or $2\times10^9$ CFUs per gram.

In some exemplary aspects, a food product, beverage, dietary supplement or other vehicle for administering MB40 to a human or animal according to any of the embodiments described herein may comprise at least one bacterial cell or spore having genomic DNA that is at least 95%, 96%, 97%, 98%, or 99% identical to the genomic DNA of the *Bacillus subtilis* MB40 which has been deposited under ATCC Accession Number PTA-122264. In some exemplary aspects, the bacterial cell or spore possesses one or more of the various functional characteristics described herein as a characteristics of MB40 (e.g., the capability to withstand high temperatures, exposure to room temperature for long periods of time, and/or pH changes). It is understood that in some aspects, these bacterial cells or spores may display any of the survivability or stability characteristics of MB40 described herein. These bacterial cells or spores may be added to a food product, beverage, supplement, pet food or other vehicle for providing MB40 to a human or pet in any of the amounts of concentrations described herein for MB40, or in other such amounts or concentrations as desired for a given application.

Methods of Preparing Food Products, Beverages, and Supplements Comprising MB40 Cells and/or Spores MB40 cells and/or spores may be added to a variety of food products, beverages, and dietary supplements. In view of MB40's increased survivability under high heat (e.g., 80° C.), extended periods of time at room temperature, and broad pH conditions, it is envisioned that MB40 cells and/or spores may be applied to most food products, beverages and dietary supplements in their current form, or with minor modifications. For example, MB40 spores may remain viable for at least 24 months at room temperature, (e.g., without refrigeration), making MB40 spores particularly well-suited for products with a long shelf life.

Processing conditions may need to be varied based on the type of food product (e.g., the amount of MB40 cells and/or spores added to a pre-processed or pre-baked composition may need to be increased in order to ensure sufficient colony-forming units in the end product). Other parameters that may be adjusted include moisture levels, temperature, and pH conditions. For example, if a composition comprising MB40 spores is to be baked at a higher temperature or for a longer time, survivability may be enhanced by increasing the moisture level of the pre-baked composition. Each of the aforementioned parameters may be varied in order to suit a desired application of the methods and compositions disclosed herein.

In certain aspects, the composition is prepared by at least one step involving the application of a high temperature for a short or sustained period of time. For example, the composition may be baked, boiled, or fried. In some aspects, MB40 spores, cells, or a mixture thereof are included in the composition prior to the application of a high temperature. For example, the MB40 cells may be dispersed in a dry mixture, a batter, or a liquid component that is then baked or mixed with additional components prior to baking.

In some aspects, the composition is heated by baking to at least 300, 325, 350, 375, 400, or 425° F. for at least 10, 15, 20, 25, or 30 minutes. In select aspects, the composition is a muffin, pancake, bread, cake, biscuit, pancake, or waffle mix comprising MB40 spores. In some aspects, the MB40 cells and/or spores are pre-mixed into the mixture prior to purchase, while in others the MB40 cells and/or spores may be provided as a separate component in a kit, to be mixed into the composition prior to heating by an end user.

In some aspects, the composition is a composition, such as a pancake comprising MB40 cells and/or spores, is cooked on a frying pan or griddle. In select aspects, the composition is cooked by heating to 375° F. (190.6° C.) for at least 2-3 minutes per side. In select aspects, the composition is formulated to retain at least 50% viability of the MB40 cells and/or spores when the mixture is heated to 375° F. (190.6° C.) for at least 2-3 minutes, twice (e.g., by cooking on each side).

Figure 5:
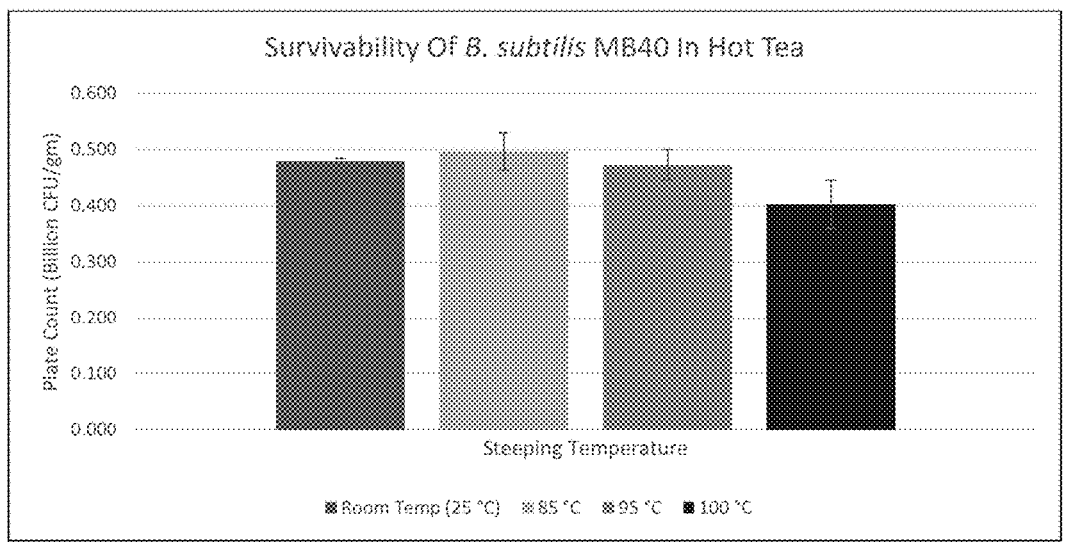
FIG. 5 is a graph illustrating survivability of *B. subtilis* MB40 in hot tea at various temperatures.

In some aspects, the composition is heated by boiling or steeping MB40 cells and/or spores in a hot solvent such as water (e.g., a tea bag comprising ground tea leaves, MB40 spores, and optionally other ingredients). In still further aspects, the composition is prepared by mixing a dry component with hot water (e.g., oatmeal comprising MB40 spores). As illustrated by FIG. 5, MB40 endospores remain substantially viable when steeped in hot water via a tea bag (e.g., at 85, 90, or 100° C.).

Foods, Beverages and Dietary Supplements Comprising MB40 Cells and/or Spores and One or More Additional Bacteria Cross streak assays have revealed that the MB40 strain is compatible with *Lactobacillus* strains such as *L. casei* and *L. acidophilus*, as well as *Bifidobacterium* strains such as *B. animalis, B. bifidum* and *B. breve*. In this assay, pure cultures of each *Lactobacillus* or *Bifidobacterium* bacterium were streaked across a culture plate perpendicular to an MB40 streak and incubated to allow growth. Over time, these cultures grew to the point where they were adjacent to each other without a gap, demonstrating compatibility or lack of inhibition between these strains.

In some aspects, a food product, beverage, or dietary supplement composition according to the disclosure may comprise MB40 cells and/or spores according to any of the aspects disclosed herein, in addition to at least one other probiotic. In some aspects, the at least one other probiotic is a probiotic bacterium (e.g., a *Lactobacillus* species such as *L. casei* and/or *L. acidophilus*). In other aspects, the bacterium is a *Bifidobacterium, Propionibacterium, Escherichia*, or *Saccharomyces* bacterial or fungal strain. In some aspects, at least two probiotic strains are present. However, additional compositions featuring multiple probiotics are also contemplated. For example, combination products may comprise refrigerated or non-refrigerated dairy (e.g., yogurt, milk, cheese), and non-dairy products (e.g., a soda, energy drink, or sports drink), fermented products, etc.

The one or more additional probiotics may be present in a food product, beverage, or dietary supplement composition in particular combinations or ratios that provide improved health benefits or other beneficial effects resulting from administration to a human or animal. For example, two strains that each promote positive gastrointestinal health or a reduction in negative gastrointestinal symptoms may be combined in a single composition in a ratio that provides a greater benefit that administration of the same amount of each probiotic separately and/or at different times. As indicated above, MB40 is compatible with several other probiotics via streak plate assays and thus may display synergistic effects when paired with these or other members of the *Lactobacillus* or *Bifidobacterium* genera, or other probiotics. The amounts, ratios and combinations of probiotics may be varied to achieve different outcomes or efficacy levels.

When MB40 is combined with at least one other probiotic, for example, in a food product, beverage, or dietary supplement, the parameters of the composition may be adjusted to provide an environment conducive to survival of both the MB40 cells and/or spores, and the one or more additional probiotics. For example, compositions featuring a *Lactobacillus* or *Bifidobacterium* may be prepared at a lower temperature suitable for these probiotics. While the MB40 strain is particularly well-suited at surviving high temperatures, compositions according to the present disclosure may be prepared at any suitable temperature (e.g., without a heating step), depending on the intended use for the composition and its components.

Pet Food Products, Beverages, and Supplements Comprising MB40 Cells and/or Spores Compositions comprising MB40 formulated for animal consumption are also provided. While the present disclosure has thus far described compositions suitable for a human, there exists an analogous need in the art for new probiotics for animals (e.g., pets or livestock). In particular, there is a need for probiotic compositions that remain viable after long periods of time in storage (e.g., dry pet food).

In some aspects, the composition comprises a wet pet food comprising MB40 cells and/or spores. In other aspects, the composition comprises a dry pet food comprising MB40 spores. In particular aspects, the composition may be a cat or dog food product, such as a bone. The pet food composition may be coated with the MB40 cells and/or spores, e.g., as an outer layer applied to dry pet food after the individual pieces have been formed, or mixed into the pet food prior to shaping. In other aspects, the composition is a liquid or dietary supplement comprising MB40 cells and/or spores (e.g., which is added to food or water in a dog bowl). In any of the above-identified aspects, the composition may comprise one or more of the following: protein, an amino acid, a plasticizer, a vitamin, and any other components known to be useful for promoting pet health and/or improving flavor. A pet food product, beverage, supplement or other vehicle for providing MB40 to a pet may be formulated to include MB40 cells and/or spores in any amounts or ranges described herein (e.g., any of the amounts and/or ranges described above in the context of food products).

Methods of Using Compositions Comprising MB40 Cells and/or Spores

Methods of administering compositions comprising MB40 cells and/or spores to individuals are also provided. For example, the disclosure provides methods of treating or reducing gastrointestinal symptoms in a human subject. In select aspects, the gastrointestinal symptoms comprise one or more of bloating, upper abdominal pain, flatulence, and/or diarrhea. In select aspects, the methods comprise administering a composition (e.g., a food product, dietary supplement, or other vehicle) comprising at least 100, 150, 200, 250, 300, 350, or 400 mg of MB40 spores, to a patient on a daily basis. In some aspects, the MB40 may be administered once-daily, twice-daily (or more frequently). In other aspects it may be once-weekly, twice-weekly, etc. In select aspects, the method comprises administering the composition at least once daily for 1, 2, 3, or 4 or more consecutive weeks, at least 6 months, at least 12 months, or other regimens that may be suitable to provide a desired effect or health benefit. The composition may be administered in any suitable format or vehicle (e.g., as a capsule, tablet, suspension, etc.). In some aspects, the MB40 may be administered to a human once per day as a capsule, tablet, suspension or other dosage form comprising $5 \times 10^9$ CFU of MB40. Other amounts and formulations may be developed to suit the particular dosage regimen and amount necessary for a given effect. For example, if administered twice-daily, each dosage form may be formulated to comprise $2.5 \times 10^9$ CFU of MB40. Liquid dosage forms may be formulated to provide similar amounts (e.g., $5 \times 10^9$ CFU of MB40) when administered. In some cases, more or less MB40 may need to be administered (e.g. if a percentage of the MB40 is expected to become non-viable during storage, a surplus amount may be included in the dosage form, e.g., capsule). In some aspects, it may be useful to administer higher or lower amounts of MB40 such as any amount between $1-10 \times 10^9$ per day (e.g., $1 \times 10^9$ per day, $2 \times 10^9$ per day, $3 \times 10^9$ per day, $4 \times 10^9$ per day, $5 \times 10^9$ per day, or $1 \times 10^{10}$ per day).

The MB40 cells and/or spores disclosed herein may also be administered to achieve other health benefits or positive effects. For example, MB40 cells and/or spores may be administered to a human or animal in an amount effective to reduce, modulate or maintain total cholesterol, triglyceride, or glucose levels. In some aspects, methods of reducing, modulating or maintaining total cholesterol, triglyceride, or glucose level may involve administration of a food product, beverage or dietary supplement comprising MB40 cells and/or spores, alone or in combination with one or more additional probiotics as described herein. In other aspects, the MB40 composition administered to achieve some or all of these effects may be any of the other food product, beverage, or dietary supplement compositions disclosed herein, provided in an amount and frequency sufficient to achieve the desired effect.

Similar methods may be employed to improve the health of animals, including house pets (e.g., cats, dogs) as well as farm animals (e.g., livestock). MB40 cells and/or spores may be administered to an animal according to a regimen similar to that used for humans, as discussed above. Alternatively, MB40 cells or spores may be added to an animal's food on a repeating or as-needed basis. In some aspects, the MB40 may be present in an amount sufficient to provide reduce gastrointestinal symptoms in the animal when administered according to a given regimen. Thus, the present disclosure provides methods of improving the health of an animal by administering an effective amount of MB40 cells and/or spores.

Cleaning Products Comprising MB40 Cells and/or Spores and Methods of Using the Same Cleaning compositions comprising MB40 cells and/or spores, and methods of making and using the same are provided. The MB40 strain is safe, non-toxic, and has antimicrobial properties, and thus may be used in a variety of environments (e.g., areas where human contact is expected). For example, MB40 may be used to establish a biofilm (e.g., on hard surface or in drains) to prevent colonization of pathogenic, malodorous or otherwise undesirable bacteria.

In some aspects, the cleaning composition is a liquid or dry cleaning composition comprising MB40 spores and/or cells. In other aspects, the cleaning composition is a liquid comprising MB40 spores and/or cells that has a pH of 2, 3, 4, 5, 6, 7, or 8, or, in other aspects a pH between 4 and 7. In some aspects, the cleaning composition comprises MB40 spores and/or cells in an aqueous solution comprising one or more surfactants, disinfectants or other components.

In some aspects, the cleaning composition is a liquid comprising $1 \times 10^{10}$ MB40 CFU/ml, optionally about $1 \times 10^6$ to $1 \times 10^8$ MB40 CFU/ml. In further aspects, the cleaning composition may have a specific concentration within this range (e.g., about $1 \times 10^8$ MB40 CFU/ml). In alternative aspects, the concentration may be higher or lower than these ranges, depending on the specific needs of a given application. In some aspects, the cleaning composition is a dry mixture comprising one or more cleaning agents and MB40 cells or spores sufficient to produce a concentration according to any of the preceding ranges when the dry mixture is added to a specified amount of solvent.

In some aspects, the cleaning composition includes one or more odor neutralizing agents (e.g., an agent that can rapidly interact, by chemical reactions, with odorous compounds to produce odorless compounds). Exemplary odor neutralizers include propylene carbonate, citrate, sodium bicarbonate, and sodium carbonate. In some aspects, the odor neutralizer is present in an amount of 1-15 wt. % of the composition.

Other components that may be used in the cleaning compositions include detergents, surfactants, fragrances, and dyes. Surfactants can wet and emulsify insoluble waste materials present in the treated system such as grease, improving cleaning efficacy. Furthermore, surfactants can be used to break down insoluble wastes therefore increasing the availability of them to degradation by enzymes produced by the MB40 or other enzymes included in the cleaning composition. Suitable surfactants may be nonionic or ionic. In select aspects, the surfactant is present in an amount of 0-8 wt. %, such as 0-6 wt. % of the cleaning composition.

In some aspects, the cleaning composition is formulated to open clogged or slow drains, comprising a stable suspension of MB40 cells or spores, surfactant(s), and optionally preservatives or fragrances, in an aqueous medium with, for example, a pH of approximately 2 to 7.

In other aspects, the cleaning composition is formulated for disinfection and may comprise, in an exemplary aspect, MB40 spores suspended in solvent comprising one or more surfactants, disinfectants (e.g., antimicrobial agents, antifungal agents, compounds that inhibit the growth and/or reproduction of one or more microorganisms). For example, the disinfectant may inhibit or eliminate growth of pathogenic microorganisms such as C. perfringens, which are becoming an increasing concern for hospitals and other medical facilities. In a general sense, a disinfectant may be any compound that inhibits, reduces, or eliminates an undesirable microorganism (selectively or as a broad spectrum agent). In some aspects, the disinfectant is a compound that does not inhibit, reduce, or eliminate MB40 cells and/or spores. In other aspects, compositions comprising such agents may be formulated in a manner that preserves efficacy (e.g., by including such compounds in a concentration that is ineffective on the suspended MB40).

Cleaning compositions such as those described herein may be used to disinfectant a surface (e.g., in a hospital setting). Upon application, the surfactant component functions to clean the surface by removing dirt, grease, etc. and assists with disinfecting the surface. The disinfectant treats the surface by killing pathogenic or undesirable bacteria, while the MB40 spores and cells colonize the surface, in some cases by forming a biofilm, resulting in the establishment of a dominant microbial population that inhibits the growth of pathogens through substrate competition, etc.

In some aspects, the cleaning compositions disclosed herein are applied to a hard or porous surface of a floor, room, or fixture. In some aspects, the compositions are applied to a rug, sink, faucet, toilet, or drain. It is contemplated that the disclosed compositions may be used in any number of environments where cleanliness is desirable, and more particularly in a hospital or related setting where reducing exposure to harmful microbes is a priority. It is further understood that the concentrations and combinations of agents in the compositions may be modified to suit a given application (e.g., increasing the amount of surfactant, disinfectants, and/or MB40 concentration to provide a more effective cleaning composition).

Compositions for Inhibiting Microbial Pathogens

Compositions according to the present disclosure may be used to inhibit the growth of pathogenic microbes (e.g., harmful bacteria). In particular, compositions comprising MB40 may be useful to inhibit the growth of *Staphylococcus* species (e.g., *S. aureus*, and methicillin-resistant *S. aureus* "MRSA" strains), *Streptococcus* species (*S. pneumoniae*), Lystaia *Listeria* species (e.g., *L. monocytogenes*), *Campylobacter* species (e.g., *C. jejum*), and *Clostridium* species (e.g., *C. perfringens*).

Antimicrobial compositions comprising MB40 have been tested using cross streak assays against multiple pathogenic bacteria, as described in Example 7. The results show that MB40 displays the ability to inhibit pathogenic members of at least several bacterial genera. These results validate MB40's usefulness in disinfectant and cleaning compositions, and suggest an additional basis for its probiotic effects. As such, compositions comprising MB40, as described herein, may be prepared and used as an antimicrobial treatment. For example, such compositions may be administered to an animal or human, or applied to a surface or area in order to inhibit the growth of a pathogenic bacteria. Antimicrobial compositions for administration to a human or animal may be delivered as part of a supplement, food product, beverage. In some aspects, it may be delivered via a tablet, capsule, spray or suspension as described herein. Antimicrobial compositions suitable for application to a surface or area may comprise a liquid, dry mixture, powder or any other vehicle suitable for administering bacterial cells or spores.

In some aspects, inhibitory compositions may comprise a combination of MB40 with one or more other probiotics or other microbes known to display antimicrobial effects. For example, a combination may include MB40 and a second non-pathogenic bacteria known to inhibit one or more pathogenic microbes (e.g., MRSA). The combinations may be formulated and/or selected to provide an additive or synergistic antimicrobial effects against one or more pathogenic bacteria. In some aspects, the pathogenic bacteria is a species selected from one of the following genera: *Staphylococcus* (e.g., *S. aureus*, MRSA *S. aureus*), *Enterococcus* (e.g., *E. faecalis*), *Listeria* (e.g., *L. monocytogenes*), *Salmonella* (e.g., *S. typhimurium*), *Streptococcus* (e.g., *S. pneumoniae*), *Pseudomonas* (e.g., *P. aeruginosa*), *Campylobacter* (e.g., *C. jejuni*), *Clostridium* (e.g., *C. difficile, C. perfringens*), *Klebsiella* (e.g., *K. pneumoniae*) *Escherichia* (e.g., *E. coli*), *Acinetobacter* (e.g., *A. baumannii*), *Aeromonas* (e.g., *A. hydrophila*), *Pasteurella* (e.g., *P. multocida*), or *Bordetella* (e.g., *B. pertussis*).

Deposit of Biological Material

The *Bacillus subtilis* strain identified as MB40 was deposited under the terms of the Budapest Treaty on Jun. 24, 2015 with the American Type Culture Collection (ATCC), 10801 University Boulevard, Manassas, Va. 20110-2209, U.S.A., under accession number PTA-122264.

The following non-limiting examples are provided to further illustrate the embodiments disclosed herein.

EXAMPLES

Example #1

Baked Muffins

MB40 survivability was evaluated in the context of a baked muffin preparation. $5 \times 10^9$ CFU/gram of MB40 spores were added to a batch of dry store-bought muffin batter mix according to the product directions, the muffin batter mix comprising: enriched flour (wheat flour, niacin, iron, thiamin mononitrate, riboflavin, folic acid), canned wild blueberries (blueberries, water), sugar, corn syrup, partially hydrogenated soybean and/or cottonseed oil, modified corn starch, leavening (baking soda, monocalcium phosphate, sodium aluminum phosphate), salt, corn starch, distilled monoglycerides, xanthan gum, cellulose gum, natural and artificial flavor, dried cultured cream.

After mixing these dry ingredients, ¾ cup milk, ¼ vegetable oil and 2 eggs were added to the dry ingredients and mixed to prepare a batter. At this point, a 20 gram sample was collected (3×) from the batter and used to perform total plate count (TPC). Thereafter, approximately ¼ cup (~45 grams) of batter was weighed out into muffin baking cups, which were then transferred to a muffin baking pan. The muffins were baked at 350° F. for 15 minutes then allowed to cool. The post-baking weight of the muffins was measured to determine average water loss. Finally, a TPC was performed for each muffin (by hydrating the entire muffin in a blending jar containing 180 mL Butterfield's buffer, blending each muffin for 2 minutes and then performing a serial dilution).

Random sampling of batter mix as described above shows an average TPC of 5.36 billion CFU/gram with relatively low percent standard deviation of 5.5%. This illustrates that MB40 spores can easily be mixed into muffin mix flour and remain homogeneous as the mix is hydrated without any spore viability loss. The post-baking analysis of MB40 activity shows an average TPC of 3.55 billion CFU/gram after accounting for water loss during baking across three separate baking studies with an average percent standard deviation of only 12.7%.

Figure 4:
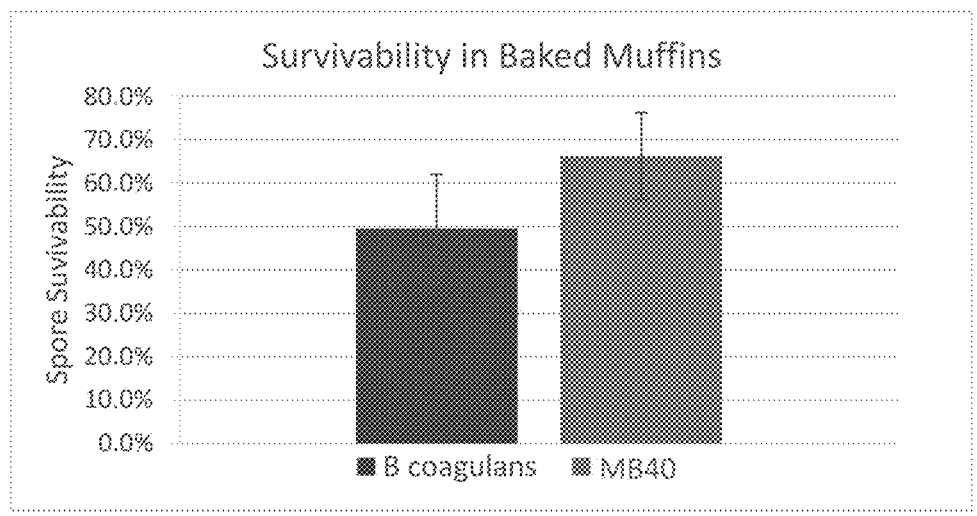
FIG. 4 is a graph illustrating survivability of *B. subtilis* MB40 contained in baked muffins compared to survivability of *B. coagulans*.

Taken together, the pre- and post-baking MB40 activity analysis indicates an MB40 survivability rate of 66% via the parameters set forth. Under identical conditions (except for a starting concentration of $1 \times 10^9$ CFU/g), *B. coagulans* spores displayed a survivability rate of only 50%. As such, MB40 has been demonstrated to survive conditions typical for baked goods and superior results compared to a similar *Bacillus* species. The results of this experiment are summarized in FIG. 4.

Example #2

Hot Tea

MB40 survivability was evaluated in the context of a hot tea preparation.

Several store-bought orange pekoe and pekoe cut black tea teabags were carefully opened and inserted with 1 gram of MB40 spores before resealing by stapling. One teabag served as a control and was steeped in 250 gram of room temperature water. Three experimental teabags were concurrently steeped for 4 minutes in 250 grams of 85° C., 95° C., or 100° C. water. A Total Plate Count (TPC) was performed in afterward to determine the survivability of MB40 in these hot beverages at the selected temperatures. The results of this study are illustrated in FIG. 5.

The MB40-containing teabag steeped in boiling water (100° C.) for 4 minutes showed 84% survivability via TPC. Similarly, the MB40-containing teabag steeped in water at 95° C. and 85° C. showed a slight improvement in survivability at 98.5% and 100%, respectively. The high temperature steeping survivability result was calculated on the basis of an average of 3 sets of TPCs. Replication of this experiment has validated these survival statistics, with a 95% average survival rate observed for MB40. These results demonstrate that MB40 is a viable probiotic that may be included in hot beverages. In contrast, a competing product containing *B. coagulans* tested under these same conditions displayed only 78% average survival rate.

Example #3

Oatmeal

MB40 survivability was evaluated in the context of a hot oatmeal preparation.

For this study, ½ cup of whole-grain rolled oats was mixed with MB40 to produce a dry composition with $1\times10^9$ MB40 CFU/gram. This dry mixture was then combined with 1 cup of water in a Pyrex bowl and blended, with three 20 gram samples removed and preheated to room temperature for a TPC. The Pyrex bowl was then microwaved for 1:45 minutes, allowed to cool for 2 minutes, and blended once more. Three additional 20 gram samples were removed to perform a post-heating TPC. MB40 activity analysis via the TPC assay indicates that the vast majority (76%) of the spores remained viable post microwaving in the hot oatmeal preparation, demonstrating MB40's ability to withstand heating times typical for microwave cooking of a moist food preparation.

Example #4

Pancake

MB40 survivability was evaluated in the context of a griddled pancake preparation.

For this study, $1\times10^9$ CFUs/gram of MB40 was mixed with 2 cups of store-bought instant pancake flour mix, with three 20 gram samples isolated in order to perform a TPC assay on the pre-cooked mixture. At this point, 1 cup of milk and 2 eggs were combined with the dry mixture and agitated to prepare a semi-liquid pancake batter, with three additional 50 gram samples collected for a second TPC assay. The batter was then weighed and cooked on electric pancake griddle at 375° F. (190.6° C.) for 2-3 minutes on each side (until gold brown). After cooking was complete, the pancakes were each collected and weighed to measure moisture loss and then subjected to a TPC assay to determine the post-cooking amount of CFUs present in each pancake. For this assay, each pancake was hydrated in 180 mL 3M Butterfield's buffer 10 minutes after the cooking stage had completed. Results from the TPC assays indicate that approximately 54% of MB40 CFUs applied to the pancake remain viable following the cooking process. These results demonstrate MB40's ability to survive relatively high heat (e.g., 375° F.) for short periods of time on a stovetop in a flour-based food product. Therefore, it is evident that MB40 may be added to other food products and/or flour-based products exposed to heating conditions (e.g., bread).

Example #5

Syrup

Figure 6:
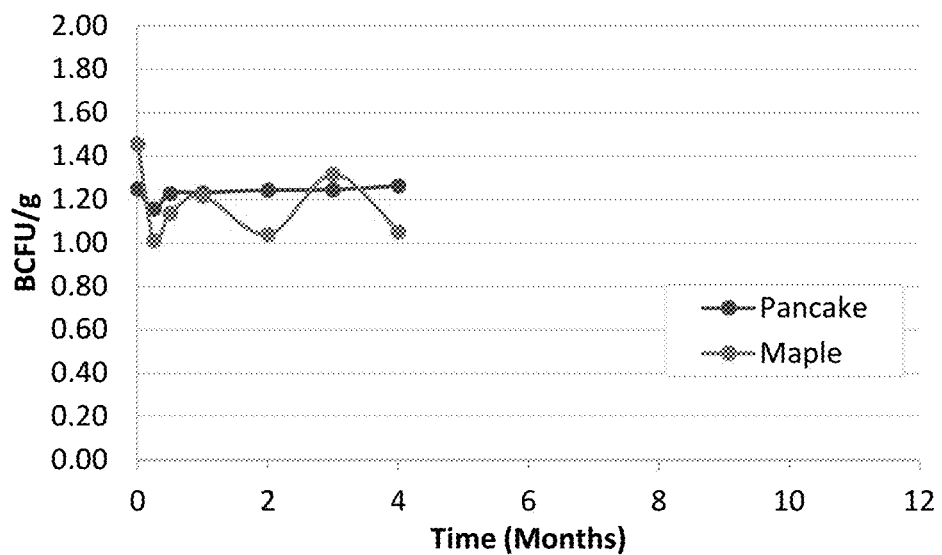
FIG. 6 is a graph illustrating survivability of *B. subtilis* MB40 in syrup.

MB40 spores were tested to evaluate long-term survivability in syrup. Specifically, MB40 spores were added to maple and pancake syrup to achieve a final concentration of $1\times10^9$ CFU/gram. The syrup samples were then stored for 4 months at room temperature, with samples taken at one week, two weeks, and then monthly for the remaining four months of the study. Samples were subjected to TPC analysis to determine the number of surviving CFUs in each sample. The results of this experiment are summarized in FIG. 6. As shown by this graph, MB40 displayed excellent shelf stability during the entire four month period, with minimal changes in viability observed at each of the assayed time points.

Example #6

Ice Cream

Figure 7:
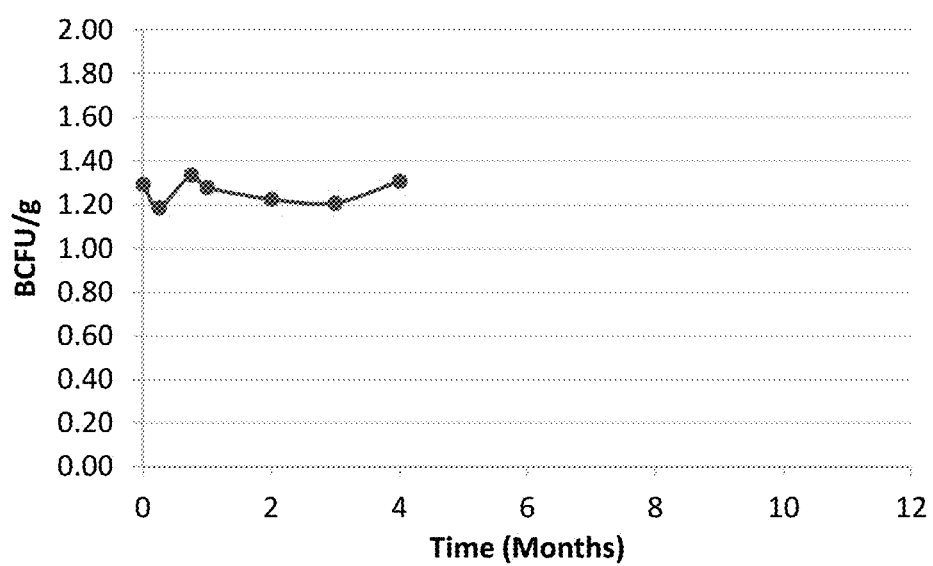
FIG. 7 is a graph illustrating survivability of *B. subtilis* MB40 in ice cream.

MB40 spores were tested to evaluate long-term survivability in ice cream (i.e., an exemplary frozen dairy product). Specifically, MB40 spores were added to store-bought vanilla ice cream to achieve a final concentration of $1\times10^9$ CFU/gram. The ice cream samples were then stored for 4 months at −18° C. (0° F.), with samples taken at one week, two weeks, and then monthly for the remaining four months of the study. Samples were subjected to TPC analysis to determine the number of surviving CFUs in each sample. The results of this experiment are summarized in FIG. 7. As shown by this graph, MB40 displayed excellent shelf stability during the entire four month period, with minimal changes in viability observed at each of the assayed time points. Follow-up studies of these samples confirm that MB40 has a 99% average survival rate under these conditions over twelve months of storage.

Example #7

Mechanically Blended Powders

Figure 8A:
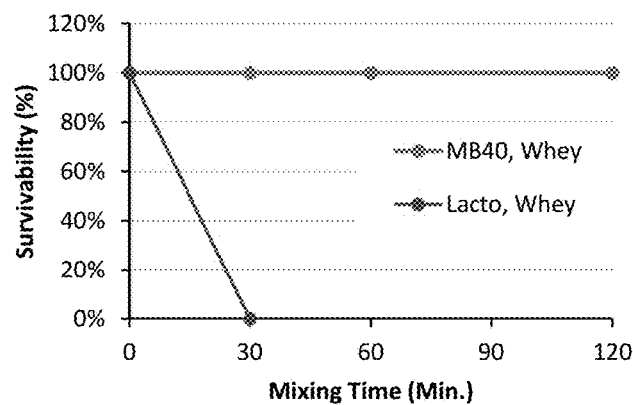
FIGS. 8A and 8B are graphs illustrating survivability of *B. subtilis* MB40 in mechanically blended whey flour (FIG. 8A) and peanut flour (FIG. 8B), as well as comparative data for *L. acidophilus* (Lacto).
Figure 8B:
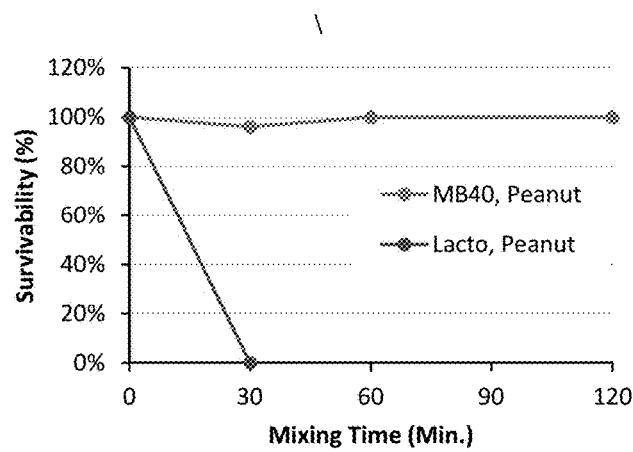

In this study, the MB40 strain was evaluated for survivability in mechanically separated powders, specifically whey flour and peanut flour. MB40 spores were added to samples of both flours to achieve a final concentration of $1\times10^9$ CFU/gram. A parallel set of samples were prepared using *L. acidophilus* as the inoculant. All four samples were mixed for two hours using a consumer-grade mechanical blender. Samples were taken at the 30, 60, 90 and 120 minute time points and subjected to TPC assays to determine the number of surviving CFUs in each sample. The results of this study are summarized in FIGS. 8A and 8B. As shown by these graphs, approximately 100% of MB40 CFUs survived the entire 2-hour mixing process, while the *L. acidiphilus* survival rate decreased to zero within the first 30 minutes. As shown by this study, MB40 is highly compatible with mechanical blending, unlike *L. acidophilus*. As a result, it may be used in products prepared by mechanical mixing, such as powdered formulations (e.g., protein powders).

Example #8

Cross Streak Test

In this study, the MB40 strain was evaluated for compatibility with probiotic *Bifidobacterium* strains. A stock of each of three *Bifidobacterium* (*Bifidobacterium animalis*, *Bifidobacterium breve*, and *Bifidobacterium bifidum*) were streaked to a MRS plate, supplemented with 0.05% L-cysteine, from a frozen culture. The streaked plate was then grown anaerobically at 35±2° C. for 48 hours. A stock MB40 culture was streaked to a TSA plate and incubated overnight at 35±2° C. A single colony was used to streak the center of a second supplemented MRS plate. An MB40 sample was streaked perpendicular to the center streak starting from the *B. animalis* streak moving toward the edge of the plate. Analogous cross streak plates were prepared for MB40 paired with *B. breve* or *B. bifidum*. In each case, the plates were then incubated anaerobically at 35±2° C. for 48 hours and then were viewed. No or very little space was observed between the center *Bifidobacterium* streak and the perpendicular MB40 streaks, indicating that MB40 is compatible with each of these strains in an in vitro setting. This assay illustrates MB40's compatibility with other probiotic strains.

Figure 9A:
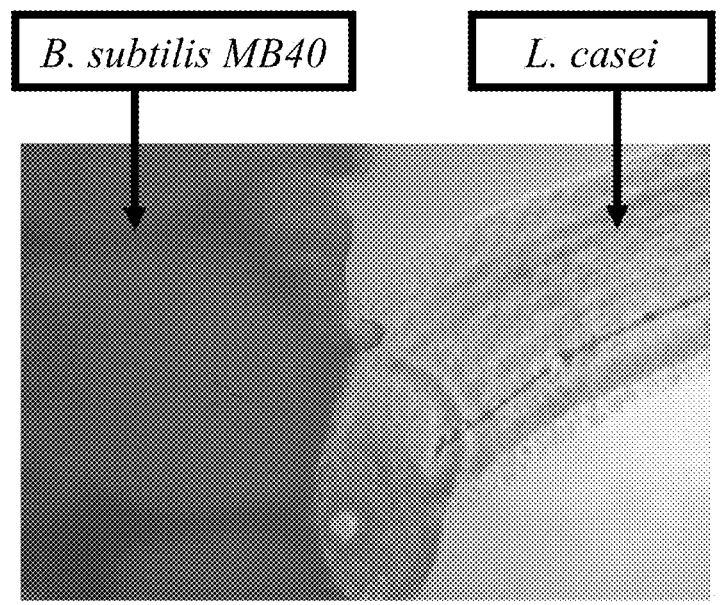
FIGS. 9A and 9B are photographs showing the results of a cross streak assay wherein a culture plate was streaked with *B. subtilis* MB40, *L. casei*, and *L. acidophilus*, illustrating compatibility between MB40 and both *Lactobacillus* species.
Figure 9B:
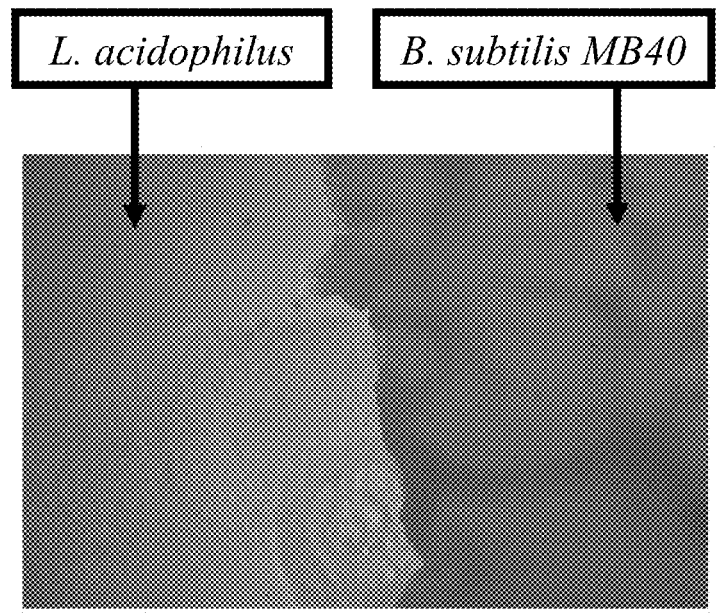

Similar assays were performed using *Lactobacillus* strains. The results of these assays is shown in FIGS. 9A and 9B. MB40's compatibility with multiple probiotics provides options for compositions comprising one or more additional probiotics.

Example #9

Methods of Using MB40 to Reduce Gastrointestinal Symptoms

MB40 was evaluated to determine whether it could effectively reduce gastrointestinal symptoms in a human following oral administration of an MB40 supplement. In this four week study, the *B. subtilis* MB40 (250 mg) was administered for 21 days BID while the placebo was administered orally twice daily (Day 1 through Day 7) with 240 mL of water. Enrolled subjects received training on gastrointestinal (GI) questionnaires, a Bristol Stool Chart diary and a 7-day supply of placebo product. The first dose of test product was taken in the at the testing facility and subjects were discharged following completion of Day 1 study procedures. Subjects returned on Days 8, 15, 22 and 29 to assess Study Product compliance and were assessed for any adverse events. Subject GI questionnaires and stool reports were reviewed at each visit and subjects received the next weekly supply of study product (*B. subtilis* MB40) along with GI questionnaires, Bristol stool chart diary for the next week. The final visit was on Day 29, following completion of the 42 doses of test product.

Figure 10:
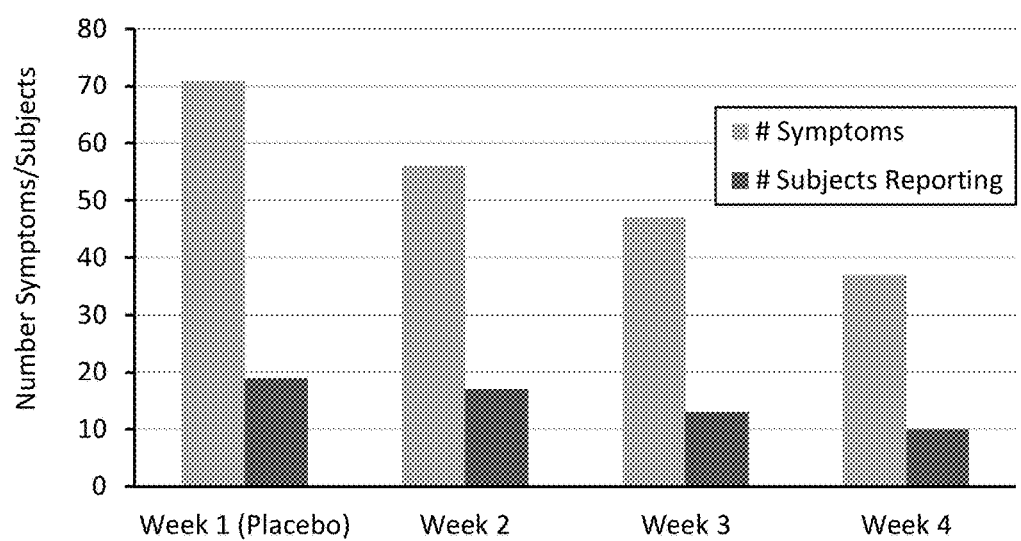
FIG. 10 is a graph illustrating clinical data from a study where *B. subtilis* MB40 was administered to human patients experiencing gastrointestinal disorder symptoms.

During the first week, a placebo was administered and 71% of the 19 study participants reported symptoms. The participants received the MB40 strain during weeks 2 through 4. As illustrated by the graph in FIG. 10, the percentage of participants reporting symptoms steadily decreased over time: 70% during the placebo week; 63% during week 2 ($1^{st}$ dose of probiotic); 48% during week 3; and 37% during week 4. Moreover, no serious adverse events were reported, indicating that the MB40 strain is safe and well tolerated over a 21-day period, in addition to displaying evidence of effectiveness as a treatment for reducing GI symptoms.

Example #10

Cross Streak Assays Used to Evaluate MB40's Potential to Inhibit the Growth of Pathogenic Bacteria To conduct this assay, an individual MB40 colony was streaked in a line down the middle of either Tryptic Soy Agar (TSA) plates (Becton Dickinson; Lot No. 4050329), TSA+ 5% sheep blood plates (Remel; Lenexa KS; Lot No. 473696), or Supplemented Brucella Agar plates (Remel; Lot No. 478124). A total of three plates were prepared. After streaking the MB40 down the middle of the plates, plates were incubated at 32° C. for 48 hr.

A 0.5 McFarland standard was prepared in Trypticase Soy Broth. Using a 10 µL calibrated loop (Becton Dickinson), each inoculum was streaked perpendicular up to, but not touching, the MB40 streak. Test bacteria were cross-streaked against the MB40 isolate per test plate. Each cross-streaked test isolate was streaked onto 3 separate MB40 test plates to allow for measurement of inhibition in triplicate. All cross-streaked plates were incubated at 32° C. for 24 hr except for the following isolates as noted below: *Aeromonas* were incubated at room temperature for 24 hr. *C. jejuni* was incubated at 32° C. for 48 hr in BD Gaspak EZ Anaerobe containers (Becton Dickinson). Each container was loaded with three BD Gaspak EZ Campy sachets (Becton Dickinson) to establish the microaerophilic atmosphere. Anaerobes were incubated at 32° C. for 48 hr in BD Gaspak EZ Anaerobe containers (Becton Dickinson). Each container was loaded with three BD Gaspak EZ Anaerobe sachets (Becton Dickinson) to establish the anaerobic atmosphere and a BBL Dry Anaerobic Indicator Strip (Becton Dickinson) to monitor anaerobiosis. Prolonged incubation (46 hours) was necessary for *L. monocytogenes*, *S. pneumoniae*, and *P. multocida* when grown on TSA due to poor growth at 24 hr.

Zones of inhibition were then measured in millimeters from the edge of growth from the center MB40 streak to the beginning of growth of the test pathogen using calipers. The median value from the triplicate measure was determined. The results of this assay indicate that MB40 demonstrates antimicrobial effects against members of several pathogenic genera, including *S. aureus*, methicillin-resistant *S. aureus* (MRSA), vancomycin-intermediate *S. aureus* (VISA), vancomycin-resistant *S. aureus* (VRSA), linezolid-resistant *S. aureus*, vancomycin-resistant *E. faecium* (VRE), linezolid-resistant *E. faecium*, *S. pneumoniae*, *C. jejuni*, and *C. perfringens*). These results suggest a possible basis for its probiotic effects and its usefulness in health-promoting, disinfectant and cleaning compositions, as disclosed herein.

Example #11

Protein Hydrolysis Assay Used to Evaluate MB40's Potential to Hydrolyze the Protein Content of an Over-the-Counter Meal Replacement Nutritional Shake Drink In order to evaluate the potential for MB40 to germinate in a nutritional beverage, an over-the-counter meal replacement nutritional shake drink was inoculated with MB40 and incubated at 37° C., with filtrate samples periodically collected and analyzed for the presence of free amino acids and by SDS-PAGE. The results of this assay demonstrate that MB40 can germinate and reach log phase within the first 8 hours when grown in a liquid media comprising an over-the-counter meal replacement nutritional shake drink.

Figure 11:
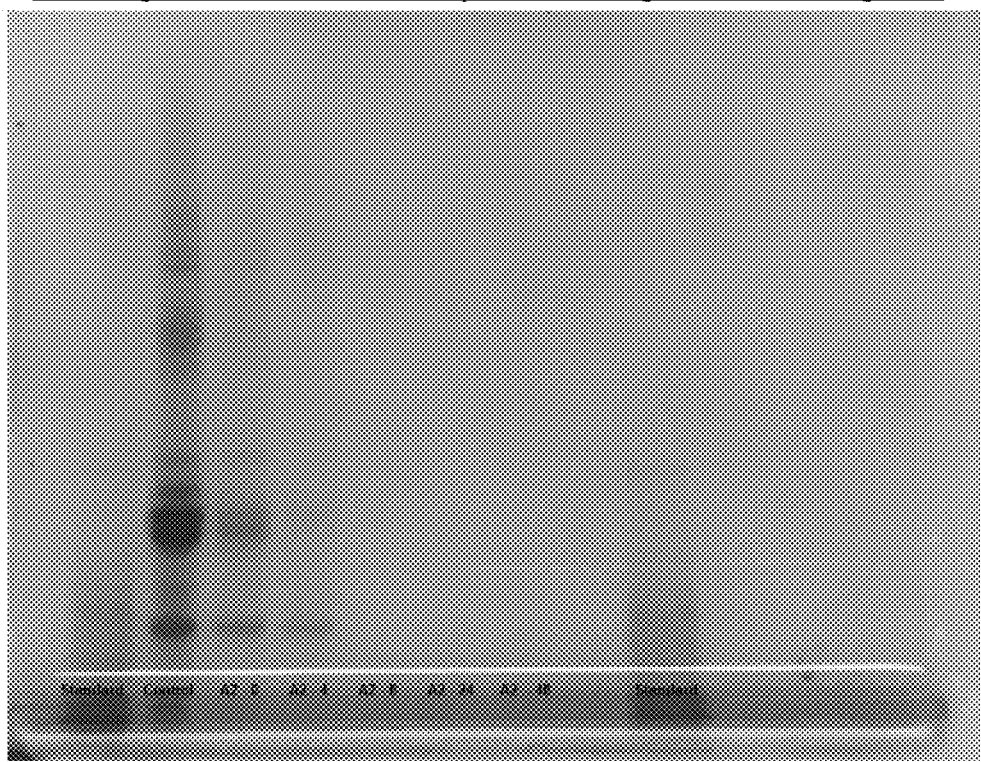
FIG. 11 is a photograph of an SDS-PAGE gel demonstrating *B. subtilis* MB40's ability to hydrolyze the protein content of an over-the-counter meal replacement nutritional shake drink.
Figure 12:
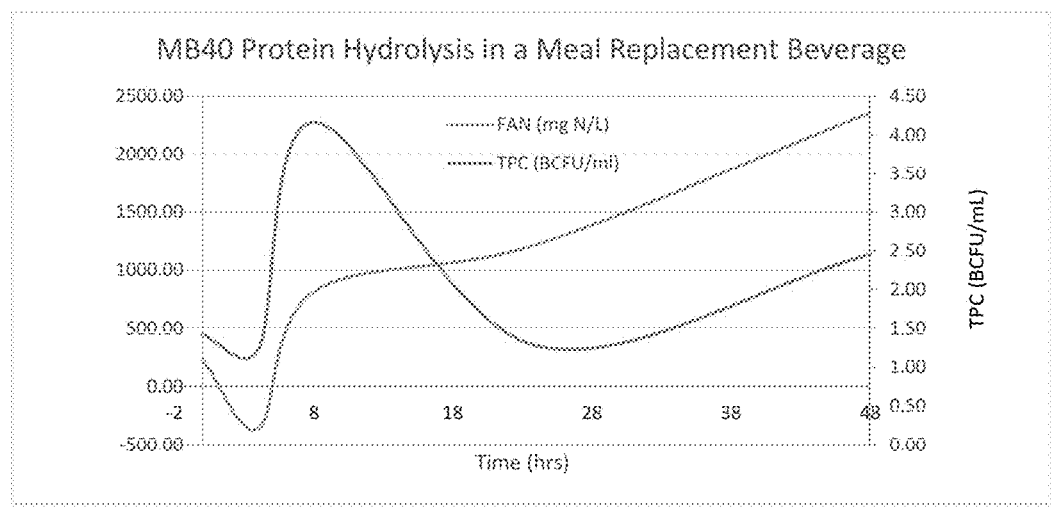
FIG. 12 is a chart summarizing total plate count ("TPC") and free amino acid ("FAN") analyses performed on *B. subtilis* MB40 cells collected after incubation in an over-the-counter meal replacement nutritional shake drink.

The following protocol was used. Approximately 100 mL of an over-the-counter meal replacement shake (pH 7+/−0.3) was dispensed into sterile 500 mL baffled flasks. An MB40 inoculant was prepared by hydrating MB40 in Butterfields' Buffer (20 gm into 180 mL), blending the MB40 for 2 minutes, and adjusting the pH to approximately 8.5 using NaOH. Approximately 10 g of a 1:10 dilution of this inoculant preparation was added to the flasks and incubated at 37° C./200 rpm for 48 hours, with 15 mL samples collected at various time-points (0, 4, 8, 24 and 48 hours). A portion of each of the collected samples was used to perform TPC assays at each time-point, with the remainder of each sample centrifuged to isolate a filtrate sample which was then analyzed for the presence of free amino acids and by SDS-PAGE. A photograph of the SDS-PAGE gel produced during this study is illustrated by FIG. 11. As shown by FIG. 11, the protein content of the filtrate gradually decreased during the 48-hour incubation period, illustrating MB40's ability to hydrolyze proteins present in the culture medium (i.e., the meal replacement beverage). The TPC and FAN assay results are summarized on the chart provided as FIG. 12, which confirms that MB40 can germinate and reach log phase within the first 8 hours when grown in an over-the-counter meal replacement shake. Significant cell density fluctuations were noted during the TPC assay and may be attributed to a pH drop observed during the first 24 hours before gradually returning and stabilizing at a neutral pH level. The FAN analysis trend showed a constant increase in free amino acids from the 8 to 48-hour time-points. Together, these assays illustrate MB40's ability to germinate in and hydrolyze proteins contained in an over-the-counter meal replacement shake.

Example #12

MB40 Stability in a Liquid Food Formulation

Figures 13A, 13B:
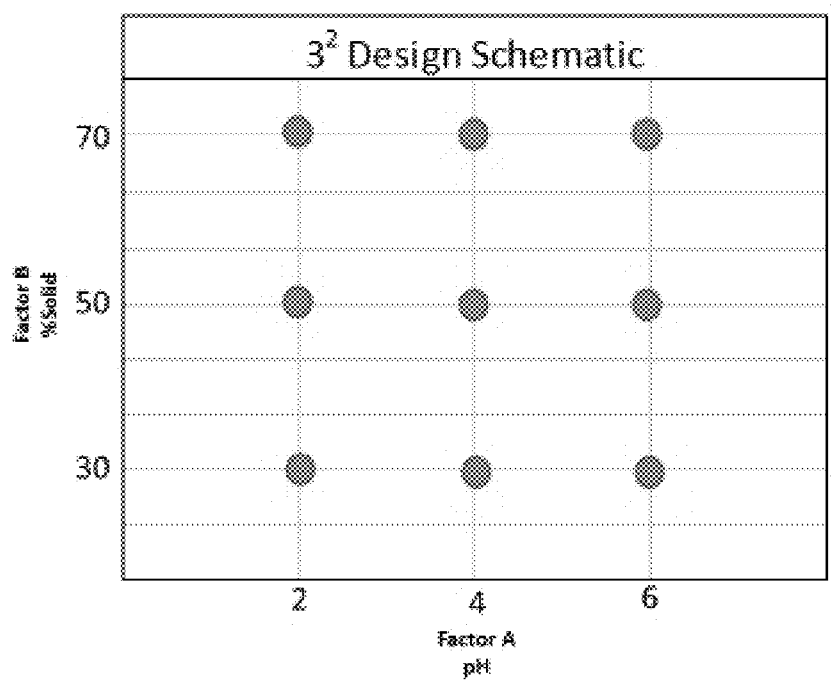
FIG. 13(*a*)-(*c*) summarizes the experimental conditions and survivability results for *B. subtilis* MB40 stored in liquid medium at various pH and percent-solid levels during a 5-month period.

MB40 was evaluated to determine the stability of this probiotic in liquid formulations at various pH and percent-solid levels over a 10-month period. The experimental design of this study is illustrated by FIGS. 13(a) and (b). Results observed at the 5-month and 10-month time points are summarized in the contour plots provided as FIGS. 13(c) and 13(d), respectively. In order to perform this analysis, 700 g of 30%, 50% and 70% solid batches were prepared in a large beaker (solids made up of 65% sugar and 35% pea protein). A preservative was then added (0.1% total weight), and sodium benzoate was added for batches with pH<5 or potassium sorbate was added for batches with pH>5. After dissolving these ingredients in water, each batch was inoculated with MB40 to produce a concentration of 1 billion CFUs/gram of total weight. Duplicate batches were prepared for each set of experimental conditions. The beakers were then set on a hot plate with stirring (or an immersion blender for high percent-solid batches), and the pH was adjusted to a preselected level using HCl or NaOH. The batches were then pasteurized at 75° C. for 1 minute, immediately cooled in ice (with stirring). Approximately 100 mL of each batch was transferred aseptically to a sterile flip-top bottle, and was stored at 25° C. The pH of each sample and TPCs were determined at the 0, 24, 48 and 96 hour time-points, and then subsequently monitored weekly for the first month and monthly after that for 10 months. Any gas production or spoilage during this period was recorded.

Figure 13C:
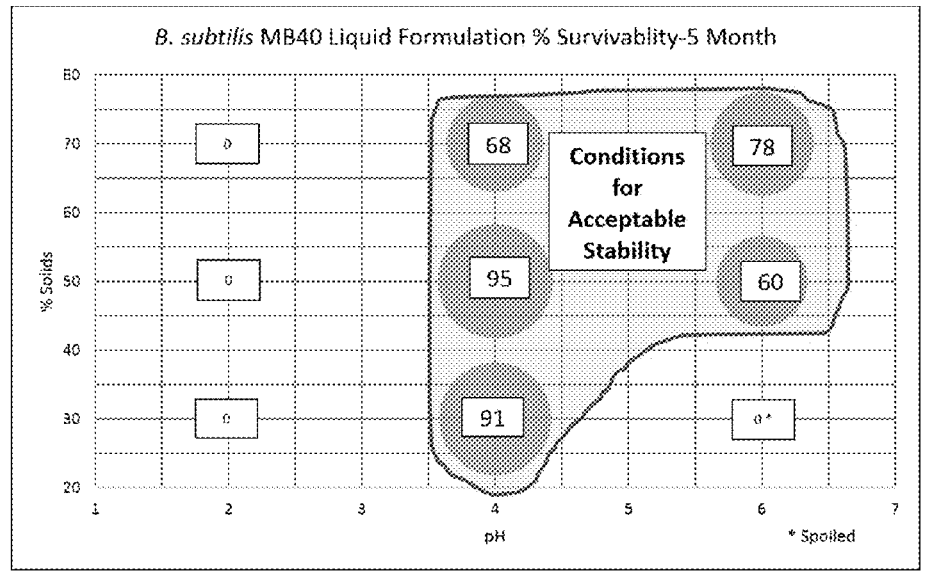

As illustrated by FIG. 13(c), TPC assays indicate that batches with a pH of 4 and above remained relatively stable at the 5-month mark with minimal activity loss. The pH of these batches remained stable with no sign of gas formation, which indicates no spore germination or spoilage occurred. All batches with at a pH of 2 showed significant loss of spore viability within the first day of total plate count monitoring. The pH 6 batch with 30% solids spoiled during the first week, preventing the collection of long-term survivability data. However, based on the other pH 6 batches displaying high survivability it is expected that pH 6 with 30% solids would display similar results. In conclusion, these results illustrate that MB40 displays good survivability within the range of pH 4 to 6 across a broad range of percent-solid levels.

Figure 13D:
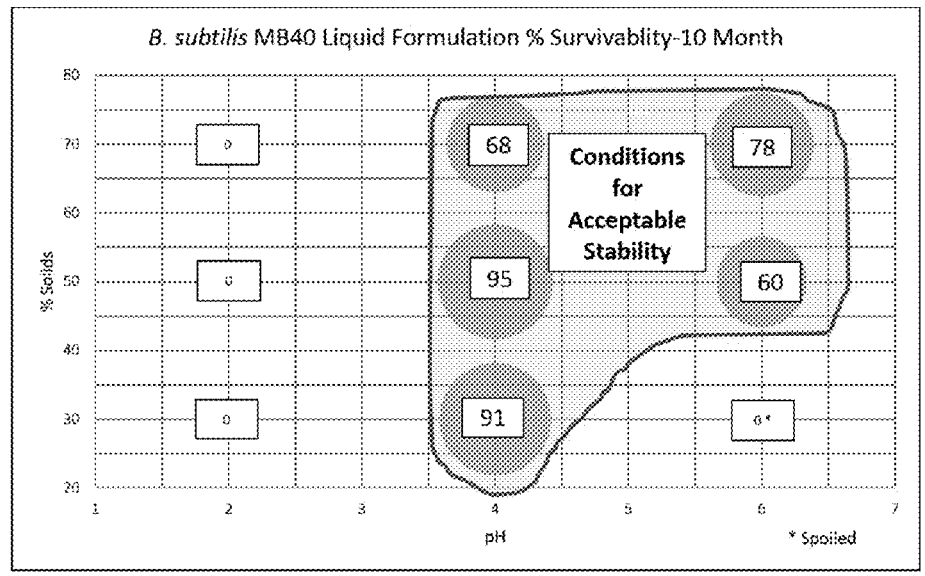

As illustrated by FIG. 13(d), TPC assays indicate that the MB40 survival rate under these conditions remains stable for at least 10 months, as the results observed at the 10-month time point are substantially identical to the results observed at 5 months. These results demonstrate that it is possible to incorporate MB40 into products with a pH ranging from 4 to 6.5 and ≥20% percent-solid while retaining >60% initial activity.

Example #13

MB40 Protein Degradation Under Simulated Human GI tract Conditions

MB40 was evaluated to determine the ability of this probiotic to increase protein solubility under conditions which simulate the human GI tract. High-protein foods and beverages are increasingly popular among consumers due to perceived health or dietary benefits and as a lifestyle choice. As a result, there is a need for more ways to increase the solubility and bioavailability of proteins and to remove proteins associated with allergenic reactions in food, supplement and beverage products. MB40 offers a unique way to increase digestion and increase availability of proteins consumed by a subject.

To evaluate MB40's ability to degrade proteins in the GI tract, MB40 was added to a soy meal protein matrix and held for 3 hours at the standard pH of the human stomach (pH 3) then gradually raised to a pH of 6.5. This experiential setup represents a simple in vitro model of the human stomach and intestines. Solubilized protein was measured at various times during this cycle. The baseline, or no probiotic added, was measured at the start and end of the process.

Figure 14:
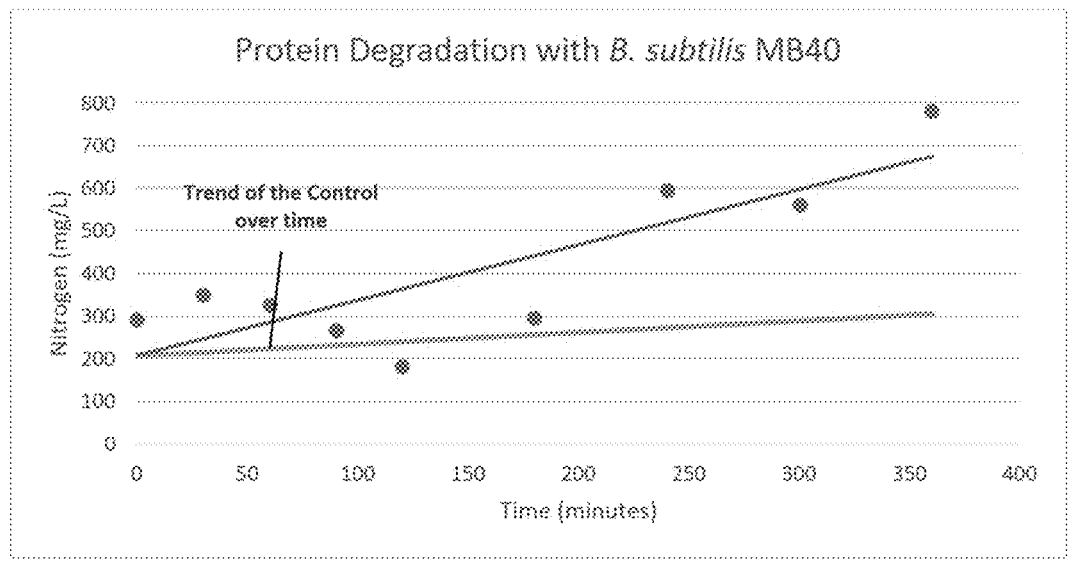
FIG. 14 is a chart summarizing results from a protein degradation assay performed with and without *B. subtilis* MB40, illustrating MB40's ability to degrade proteins under conditions which simulate the pH of the human gastrointestinal ("GI") tract.

As illustrated by FIG. 14, MB40 is capable of surviving typical stomach pH conditions, and then germinating in the GI tract where it can provide enhanced digestion of protein throughout the GI tract. An approximate comparison of the MB40 and control trend lines reveals that MB40 provided a four-fold increase in protein degradation after 5 hours compared to the control (untreated) sample.

Example #14

MB40 Stability in a Gummy Preparation

MB40 was evaluated to determine the stability of this probiotic in gummy (e.g., gelatin-based) formulations. Gummy preparations are a popular format for dietary supplements. Gummy-based vitamin, calcium and probiotic supplements are commercially available. However, some agents and in particular probiotic agents, are incompatible with gummy preparations and/or manufacturing procedures used to create such preparations.

In order to determine whether MB40 is compatible with gummy preparations, several MB40-inoculated samples were prepared and evaluated by calculating survivability rates. The gummy preparations were prepared by blending together: 85 g of sugared strawberry flavored gelatin mix (28 g of gelatin+57 g of sugar and flavoring), 28 g of unflavored gelatin and 2.25 g of MB40 (weighed to give the entire gelatin mixture an average of 1 billion CFU/g). After blending this mixture in a Pyrex dish, 112 g of deionized water was added and the resulting mixture was mixed over low heat until the gelatin completely dissolved. The final temperature of the mixture at this stage was recorded as 60° C. The solution was poured into a prepared pan lined with aluminum foil and allowed to cool at room temperature for approximately 1 hour. This sheet of MB40 gummy preparation was then vacuum sealed into bags and refrigerated until colony counts for the finished product could be verified.

The gummy preparation was analyzed for spore viability using plate counts. A total of 8 plates, organized as 3 trials, were analyzed to verify that the final product had 1 billion CFU/g of viable MB40 spores. The results for each plate count and average plate counts are summarized by the table provided as FIG. 15(a).

Figures 15A, 15B:
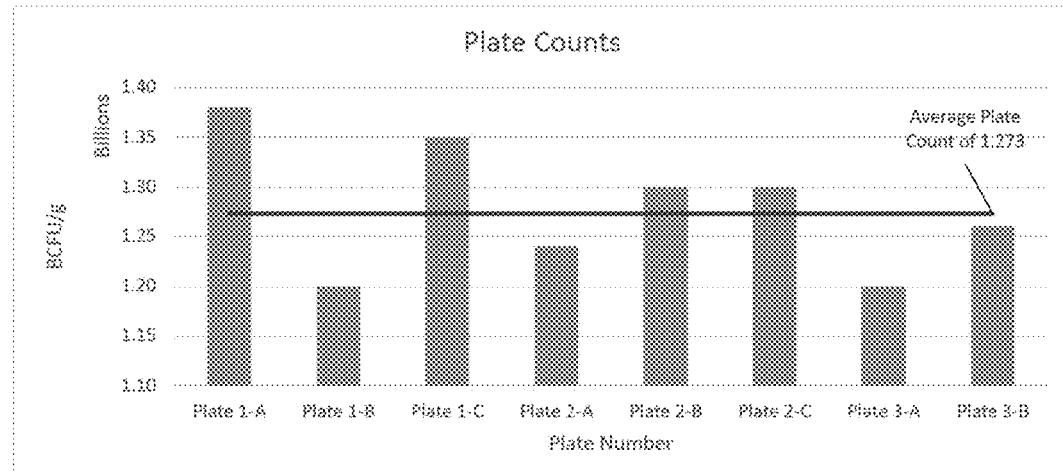
FIG. 15(*a*) is a table summarizing *B. subtilis* MB40 spore viability in eight samples of gummy (e.g., gelatin-based) preparations.

As illustrated by FIG. 15(b), when the individual plate counts are compared to the average plate count, there is a very small deviation from the mean, which in this case amounted to 1.273 BCFU/g. The results from this experiment demonstrate that MB40 may be provided as a gummy preparation which is heated up to at least 60° C. during processing without any loss of viability.

The invention claimed is:

1. *Bacillus subtilis* MB40, a sample of which has been deposited under ATCC Accession No. PTA-122264.

2. The *Bacillus subtilis* MB40 of claim 1, wherein the *Bacillus subtilis* MB40 is in the form of an endospore.

3. A probiotic composition comprising the *Bacillus subtilis* MB40 of claim 1 and at least one additional probiotic.

4. A food product comprising the *Bacillus subtilis* MB40 of claim 1 and flour.

5. The food product of claim 4, wherein the food product is a muffin, pancake, bread, cake, biscuit, pancake, or waffle.

6. The food product of claim 4, wherein the *Bacillus subtilis* MB40 is present in the food product:
 a) at a concentration of at least $1\times10^6$, $1\times10^7$, $1\times10^8$, $1\times10^9$, or $2\times10^9$ colony-forming units (CFUs)/gram;
 b) in an amount equal to at least $1\times10^6$, $1\times10^7$, $1\times10^8$, $1\times10^9$, or $2\times10^9$ CFUs/serving of the food product; or
 c) in an amount equal to at least $1\times10^6$, $1\times10^7$, $1\times10^8$, $1\times10^9$, or $2\times10^9$ CFUs/food product.

7. The food product of claim 3, wherein the at least one additional probiotic comprises a species of *Lactobacillus* or a species of *Bifidobacterium*.

8. The food product of claim 3, wherein the at least one additional probiotic comprises *Bifidobacterium animalis*, *Bifidobacterium breve*, *Bifidobacterium bifidum*, *Lactobacillus acidophilus*, or *Lactobacillus casei*.

9. A beverage comprising the *Bacillus subtilis* MB40 of claim 1 and a liquid.

10. The beverage of claim 9, wherein the beverage is a tea, juice, dairy product, soda, coffee, sports drink, or energy drink.

11. The beverage of claim 9, wherein the *Bacillus subtilis* MB40 is present in the beverage at a concentration of at least $1\times10^6$, $1\times10^7$, $1\times10^8$, $1\times10^w$, or $2\times10^9$ CFUs/gram.

12. The beverage of claim 9, further comprising at least one additional probiotic.

13. The beverage of claim 12, wherein the at least one additional probiotic comprises a species of *Lactobacillus* or a species of *Bifidobacterium*.

14. The beverage of claim 12, wherein the at least one additional probiotic comprises *Bifidobacterium animalis*, *Bifidobacterium breve*, *Bifidobacterium bifidum*, *Lactobacillus acidophilus*, or *Lactobacillus casei*.

15. A dietary supplement comprising the *Bacillus subtilis* MB40 of claim 1 and one or more of a natural or artificial sweetener, soluble fiber, insoluble fiber, flavoring agent, colorant, dye, stabilizer, preservative, anti-caking agent, vitamin, mineral, amino acid, peptide, and/or protein.

16. The dietary supplement of claim 15, wherein the dietary supplement is a powder, tablet, pill, sachet, capsule, or suspension.

17. The dietary supplement of claim 15, wherein the *Bacillus subtilis* MB40 is present in the dietary supplement at a concentration of at least $1\times10^6$, $1\times10^7$, $1\times10^8$, $1\times10^9$, $5\times10^9$, or $1\times10^{10}$ CFUs/gram.

18. The dietary supplement of claim 15, further comprising at least one additional probiotic.

19. A pet food comprising the *Bacillus subtilis* MB40 of claim 1 and one or more fatty acids, free amino acids, or a protein.

20. A method of preparing a food product comprising the *Bacillus subtilis* MB40, according to claim 1, comprising:
 dispersing a plurality of *Bacillus subtilis* MB40 cells and/or spores into a liquid, semidiquid, or dry composition;
 heating the composition to a temperature of at least 300° F. in order to produce a food product.

21. A cleaning composition comprising the *Bacillus subtilis* MB40, according to claim 1, suspended in water, and optionally including one or more of the following:
 ionic or nonionic surfactants;
 a disinfectant comprising an antimicrobial or antifungal compound;
 one or more salts;
 and/or one or more oxidizing agents.

22. A method of reducing gastrointestinal symptoms in a human or animal in need thereof, comprising administering an effective amount of the *Bacillus subtilis* MB40 of claim 1 to said human or animal in need thereof.

23. A composition comprising the *Bacillus subtilis* MB40 of claim 1, wherein the *Bacillus subtilis* MB40 is spray dried.

* * * * *